United States Patent
Ho et al.

(10) Patent No.: US 11,472,030 B2
(45) Date of Patent: Oct. 18, 2022

(54) ROBOTIC SYSTEM WITH INDICATION OF BOUNDARY FOR ROBOTIC ARM

(71) Applicant: Auris Health, Inc., Redwood City, CA (US)

(72) Inventors: Mingyen Ho, Santa Clara, CA (US); David Paul Noonan, San Francisco, CA (US); Shu-Yun Chung, San Jose, CA (US); Allen Jiang, Fremont, CA (US)

(73) Assignee: Auris Health, Inc., Redwood, CA (US)

( * ) Notice: Subject to any disclaimer, the term of this patent is extended or adjusted under 35 U.S.C. 154(b) by 147 days.

(21) Appl. No.: 16/670,349

(22) Filed: Oct. 31, 2019

(65) Prior Publication Data
US 2020/0171660 A1    Jun. 4, 2020

Related U.S. Application Data

(63) Continuation of application No. 16/141,755, filed on Sep. 25, 2018, now Pat. No. 10,464,209.
(Continued)

(51) Int. Cl.
*A61B 34/30*    (2016.01)
*B25J 9/16*    (2006.01)
(Continued)

(52) U.S. Cl.
CPC .............. *B25J 9/1666* (2013.01); *A61B 34/30* (2016.02); *A61B 34/37* (2016.02); *A61B 34/70* (2016.02);
(Continued)

(58) Field of Classification Search
CPC ......... A61B 34/70; A61B 90/03; A61B 34/30; A61B 34/37; A61B 90/361;
(Continued)

(56) References Cited

U.S. PATENT DOCUMENTS 4,921,393 A    5/1990   Andeen
5,375,588 A   12/1994   Yoon
(Continued)

FOREIGN PATENT DOCUMENTS

EP    0 830 562    7/2009

OTHER PUBLICATIONS

EP Search Report for appl. No. 18865053, dated May 17, 2021, 2 pages.
(Continued)

*Primary Examiner* — Stephen Holwerda
(74) *Attorney, Agent, or Firm* — Chang & Hale LLP

(57) ABSTRACT

Certain aspects relate to systems and techniques for surgical robotic arm setup. In one aspect, there is provided a system including a first robotic arm configured to manipulate a medical instrument, a processor, and a memory. The processor may be configured to: determine a minimum stroke length of the first robotic arm that allows advancing of the medical instrument by the first robotic arm to reach a target region from an access point via a path, determine a boundary for an initial pose of the first robotic arm based on the minimum stroke length and a mapping stored in the memory, and during an arm setup phase prior to performing a procedure, provide an indication of the boundary during movement of the first robotic arm.

30 Claims, 21 Drawing Sheets

Related U.S. Application Data

(60) Provisional application No. 62/568,733, filed on Oct. 5, 2017.

(51) Int. Cl.

| | | |
|---|---|---|
| *A61B 90/00* | (2016.01) | |
| *A61B 34/00* | (2016.01) | |
| *A61B 34/37* | (2016.01) | |
| *A61B 34/20* | (2016.01) | |
| *A61B 17/00* | (2006.01) | |
| *A61B 90/98* | (2016.01) | |
| *A61B 90/90* | (2016.01) | |
| *A61B 46/10* | (2016.01) | |

(52) U.S. Cl.
CPC ............ *A61B 90/03* (2016.02); *B25J 9/1697* (2013.01); *A61B 34/76* (2016.02); *A61B 46/10* (2016.02); *A61B 90/361* (2016.02); *A61B 90/90* (2016.02); *A61B 90/98* (2016.02); *A61B 2017/00477* (2013.01); *A61B 2034/2046* (2016.02); *A61B 2034/2051* (2016.02); *A61B 2034/256* (2016.02); *A61B 2034/302* (2016.02); *A61B 2034/303* (2016.02); *A61B 2090/376* (2016.02); *A61B 2090/3762* (2016.02); *A61B 2217/005* (2013.01); *A61B 2217/007* (2013.01); *G05B 2219/40315* (2013.01); *G05B 2219/45123* (2013.01)

(58) Field of Classification Search
CPC ........ A61B 2034/256; A61B 2034/303; A61B 2017/00477; A61B 90/98; A61B 90/90; A61B 2217/005; A61B 2090/376; A61B 2034/302; A61B 2034/2046; A61B 2217/007; A61B 2090/062; A61B 2090/061; A61B 2034/2051; A61B 2034/102; A61B 2090/3762; A61B 34/76; A61B 46/10; B25J 9/1666; B25J 9/1697; G05B 2219/40315; G05B 2219/45123

See application file for complete search history.

(56) References Cited

U.S. PATENT DOCUMENTS

| | | | |
|---|---|---|---|
| 5,402,801 A | 4/1995 | Taylor | |
| 5,540,648 A | 7/1996 | Yoon | |
| 5,746,720 A | 5/1998 | Stouder | |
| 5,865,809 A | 2/1999 | Moenning et al. | |
| 6,205,411 B1 * | 3/2001 | DiGioia, III | A61F 2/46 |
| | | | 703/11 |
| 6,279,579 B1 | 8/2001 | Riaziat | |
| 6,522,906 B1 | 2/2003 | Salisbury et al. | |
| 6,850,817 B1 | 2/2005 | Green | |
| 7,699,855 B2 | 4/2010 | Anderson | |
| 8,469,947 B2 | 6/2013 | Devengenzo | |
| 8,491,597 B2 | 7/2013 | Russell et al. | |
| 8,506,555 B2 | 8/2013 | Ruiz Morales | |
| 9,226,796 B2 | 1/2016 | Bowling | |
| 9,480,534 B2 | 11/2016 | Bowling | |
| 9,504,604 B2 | 11/2016 | Alvarez | |
| 9,561,083 B2 | 2/2017 | Yu et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,795,445 B2 | 10/2017 | Bowling | |
| 9,820,818 B2 | 11/2017 | Malackowski | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,004,562 B2 | 6/2018 | Kostrzewski | |
| 10,004,569 B2 | 6/2018 | Singh | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,154,829 B2 | 12/2018 | Henderson et al. | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,493,241 B2 | 12/2019 | Jiang | |
| 10,639,114 B2 | 5/2020 | Schuh | |
| 10,667,875 B2 | 6/2020 | DeFonzo | |
| 10,751,140 B2 | 8/2020 | Wallace et al. | |
| 10,765,487 B2 | 9/2020 | Ho | |
| 2002/0120188 A1 * | 8/2002 | Brock | A61B 5/0086 |
| | | | 600/407 |
| 2002/0193685 A1 | 12/2002 | Mate | |
| 2003/0050558 A1 | 3/2003 | Bencini | |
| 2004/0009459 A1 * | 1/2004 | Anderson | G06T 19/00 |
| | | | 703/11 |
| 2004/0106916 A1 * | 6/2004 | Quaid | A61B 34/71 |
| | | | 606/1 |
| 2004/0115606 A1 * | 6/2004 | Davies | A63B 69/0057 |
| | | | 434/258 |
| 2004/0243147 A1 * | 12/2004 | Lipow | A61B 34/74 |
| | | | 606/130 |
| 2005/0182295 A1 | 8/2005 | Soper et al. | |
| 2006/0079756 A1 | 4/2006 | Lloyd et al. | |
| 2006/0270909 A1 | 11/2006 | Davis et al. | |
| 2007/0021738 A1 | 1/2007 | Hasser et al. | |
| 2007/0144298 A1 | 6/2007 | Miller | |
| 2007/0244599 A1 | 10/2007 | Tsai | |
| 2008/0077158 A1 | 3/2008 | Haider et al. | |
| 2009/0099445 A1 | 4/2009 | Burger | |
| 2009/0088634 A1 | 5/2009 | Zhao | |
| 2009/0248037 A1 | 10/2009 | Prisco | |
| 2009/0259412 A1 | 10/2009 | Brogardh | |
| 2010/0234999 A1 | 9/2010 | Nakajima | |
| 2011/0040411 A1 | 2/2011 | Murayama et al. | |
| 2011/0060215 A1 | 3/2011 | Tupin | |
| 2011/0144479 A1 | 6/2011 | Hastings et al. | |
| 2011/0208355 A1 | 8/2011 | Tsusaka | |
| 2012/0046542 A1 | 2/2012 | Csavoy et al. | |
| 2012/0191107 A1 | 7/2012 | Tanner et al. | |
| 2013/0041509 A1 | 2/2013 | Saito | |
| 2013/0053648 A1 * | 2/2013 | Abovitz | A61B 90/92 |
| | | | 600/249 |
| 2013/0169423 A1 * | 7/2013 | Iorgulescu | G06F 3/0482 |
| | | | 340/407.1 |
| 2013/0173058 A1 | 7/2013 | Seo et al. | |

(56) References Cited

U.S. PATENT DOCUMENTS

| | | |
|---|---|---|
| 2014/0039517 A1 | 2/2014 | Bowling |
| 2014/0052154 A1 | 2/2014 | Griffiths |
| 2014/0088763 A1* | 3/2014 | Hazan .................. B25J 9/1666 700/255 |
| 2014/0142591 A1 | 5/2014 | Alvarez et al. |
| 2014/0350387 A1 | 11/2014 | Siewerdsen et al. |
| 2014/0357984 A1 | 12/2014 | Wallace et al. |
| 2014/0364870 A1 | 12/2014 | Alvarez et al. |
| 2015/0051732 A1 | 2/2015 | Grygorowicz et al. |
| 2015/0066051 A1 | 3/2015 | Kwon |
| 2015/0202015 A1 | 7/2015 | Elhawary et al. |
| 2015/0239121 A1 | 8/2015 | Takeda |
| 2015/0248121 A1 | 9/2015 | Nilsson |
| 2015/0289941 A1 | 10/2015 | Bowling |
| 2015/0323398 A1 | 11/2015 | Lauzier et al. |
| 2015/0328771 A1 | 11/2015 | Yuelai et al. |
| 2015/0374446 A1 | 12/2015 | Malackowski |
| 2016/0001038 A1 | 1/2016 | Romo et al. |
| 2016/0022189 A1 | 1/2016 | Pouteau et al. |
| 2016/0031083 A1 | 2/2016 | Embon |
| 2016/0074117 A1 | 3/2016 | Mohr |
| 2016/0100896 A1 | 4/2016 | Yu |
| 2016/0144509 A1 | 5/2016 | Gulhar |
| 2016/0158601 A1 | 6/2016 | Lee et al. |
| 2016/0206374 A1 | 7/2016 | Tyc et al. |
| 2016/0221189 A1 | 8/2016 | Nilsson |
| 2016/0270865 A1 | 9/2016 | Landey et al. |
| 2016/0279405 A1 | 9/2016 | Riley |
| 2016/0287279 A1 | 10/2016 | Bovay et al. |
| 2016/0354925 A1 | 12/2016 | Shimodaira |
| 2016/0361122 A1 | 12/2016 | Seeber |
| 2017/0007336 A1 | 1/2017 | Tsuboi |
| 2017/0007337 A1 | 1/2017 | Dan |
| 2017/0007342 A1 | 1/2017 | Kasai |
| 2017/0119481 A1 | 5/2017 | Romo et al. |
| 2017/0165011 A1 | 6/2017 | Bovay et al. |
| 2017/0165834 A1 | 6/2017 | Hares |
| 2017/0172673 A1 | 6/2017 | Yu et al. |
| 2017/0172676 A1* | 6/2017 | Itkowitz ................ A61B 90/03 |
| 2017/0172680 A1 | 6/2017 | Bowling |
| 2017/0202627 A1 | 7/2017 | Sramek et al. |
| 2017/0209073 A1 | 7/2017 | Sramek et al. |
| 2017/0245955 A1 | 8/2017 | Bowling |
| 2017/0252113 A1 | 9/2017 | Beelen et al. |
| 2017/0258529 A1 | 9/2017 | Winne |
| 2017/0274530 A1 | 9/2017 | Mottram |
| 2017/0290631 A1 | 10/2017 | Lee et al. |
| 2017/0340396 A1 | 11/2017 | Romo et al. |
| 2017/0363669 A1 | 12/2017 | Deghan Marvast |
| 2017/0367782 A1 | 12/2017 | Schuh et al. |
| 2018/0025666 A1 | 1/2018 | Ho et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0365491 A1 | 12/2019 | Yu |
| 2019/0375383 A1 | 12/2019 | Auer |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

OTHER PUBLICATIONS

EP Written Opinion for appl. No. 18865053, dated May 17, 2021, 6 pages.
Skarecky et al., 2008, Zero positive surgical margins after radical prostatectomy: is the end in sight?, Expert Review of Medical Devices, 5(6):709-717.
Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.
International Search Report and Written Opinion dated Nov. 29, 2018 in application No. PCT/US2018/052984.
CN Third Office Action for appl No. 201880073215.2, dated Dec. 27, 2021, 5 pages.
Search report for U.S. Appl. No. 18/865,053, dated May 17, 2021, 10 pages.

* cited by examiner

ROBOTIC SYSTEM WITH INDICATION OF BOUNDARY FOR ROBOTIC ARM

CROSS-REFERENCE TO RELATED APPLICATION(S)

This application is a continuation of U.S. application Ser. No. 16/141,755, filed Sep. 25, 2018, which claims the benefit of U.S. Provisional Application No. 62/568,733, filed Oct. 5, 2017, each of which is hereby incorporated by reference in its entirety.

TECHNICAL FIELD

The systems and methods disclosed herein are directed to robotic arm setup, and more particularly to providing an indication of a boundary for an initial pose of a robotic arm of a robotic system.

BACKGROUND

Medical procedures such as endoscopy (e.g., bronchoscopy) may involve the insertion of a medical tool into a patient's luminal network (e.g., airways) for diagnostic and/or therapeutic purposes. Surgical robotic systems may be used to control the insertion and/or manipulation of the medical tool during a medical procedure. The surgical robotic system may comprise at least one robotic arm including a manipulator assembly which may be used to control the positioning of the medical tool prior to and during the medical procedure.

SUMMARY

The systems, methods and devices of this disclosure each have several innovative aspects, no single one of which is solely responsible for the desirable attributes disclosed herein.

In one aspect, there is provided a system comprising: a first robotic arm configured to manipulate a medical instrument; a processor; and a memory storing a mapping of an anatomy of a patient. The mapping may comprise data regarding (i) a target region within the anatomy and (ii) a path from an access point of the patient to the target region. The memory may further store computer-executable instructions, that when executed, cause the processor to: determine a minimum stroke length of the first robotic arm that allows advancing of the medical instrument by the first robotic arm to reach the target region from the access point via the path, determine a boundary for an initial pose of the first robotic arm based on the minimum stroke length and the mapping, and during an arm setup phase prior to performing a procedure, provide an indication of the boundary during movement of the first robotic arm.

In another aspect, there is provided a non-transitory computer readable storage medium having stored thereon instructions that, when executed, cause at least one computing device to: determine a minimum stroke length of a first robotic arm that allows advancing of a medical instrument by the first robotic arm to a target region based on a mapping of an anatomy of a patient, the mapping comprising data regarding (i) the target region within the anatomy and (ii) a path from an access point of the patient to the target region, the medical instrument advanced to reach the target region from the access point via the path; determine a boundary for an initial pose of the first robotic arm based on the minimum stroke length and the mapping; and during an arm setup phase prior to performing a procedure, provide an indication of the boundary during movement of the first robotic arm.

In yet another aspect, there is provided a method of positioning a first robotic arm, comprising: determining a minimum stroke length of the first robotic arm that allows advancing of a medical instrument by the first robotic arm to reach a target region based on a mapping of an anatomy of a patient, the mapping comprising data regarding (i) the target region within the anatomy and (ii) a path from an access point of the patient to the target region, the medical instrument advanced to reach the target region from the access point via the path; determine a boundary for an initial pose of the first robotic arm based on the minimum stroke length and the mapping; and during an arm setup phase prior to performing a procedure, provide an indication of the boundary during movement of the first robotic arm.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
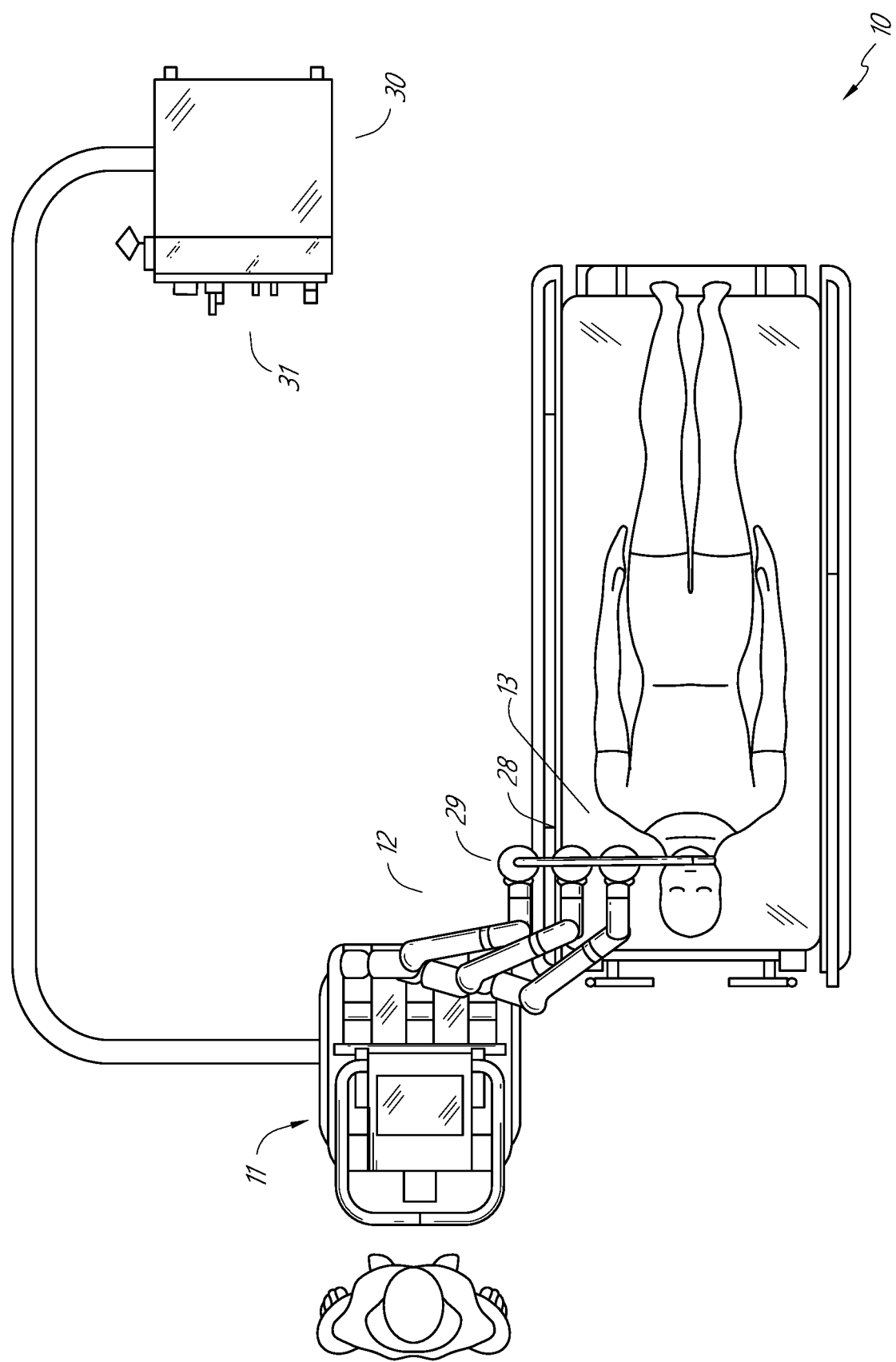
FIG. 1 illustrates an embodiment of a cart-based robotic system arranged for diagnostic and/or therapeutic bronchoscopy procedure(s).
Figure 2:
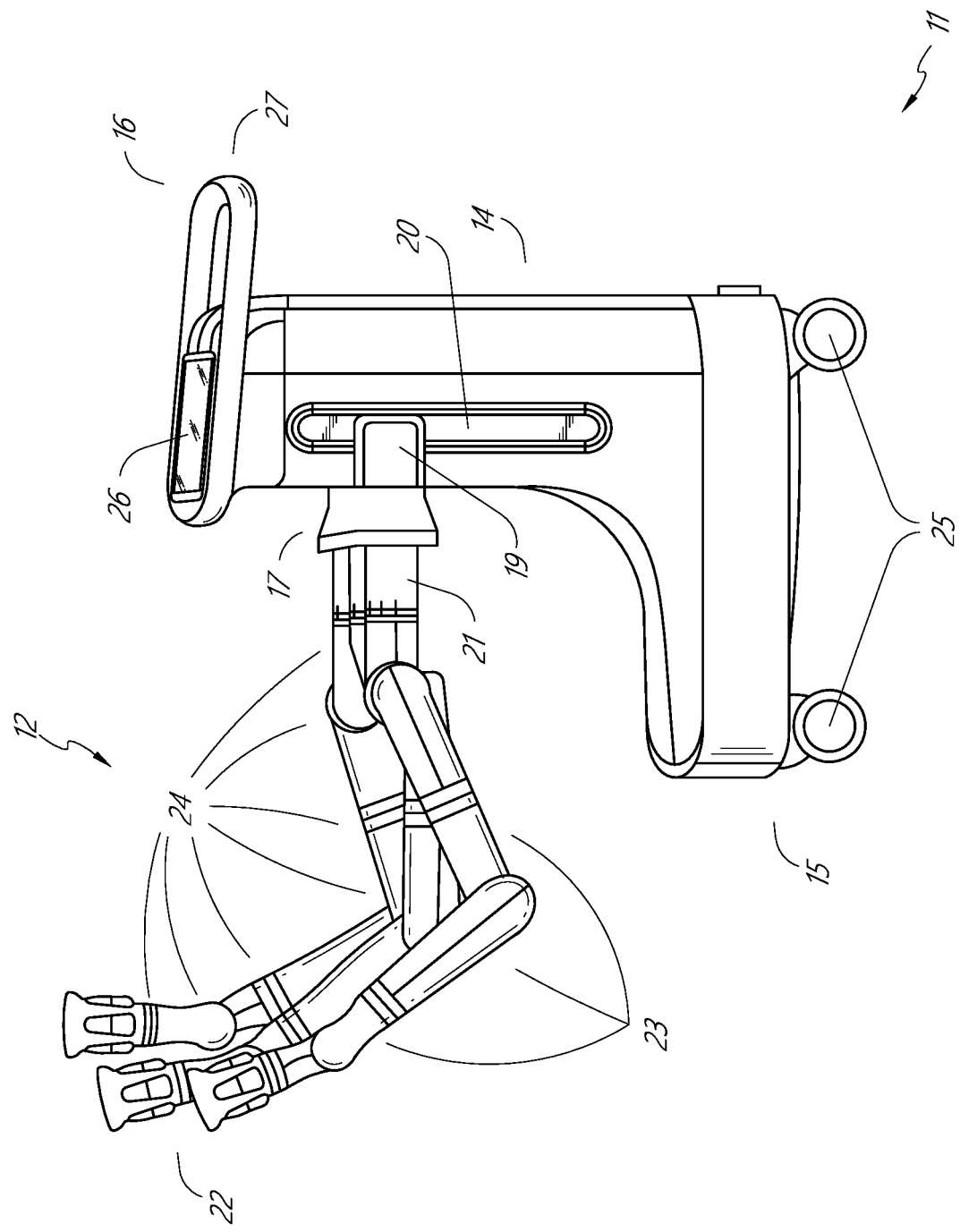
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
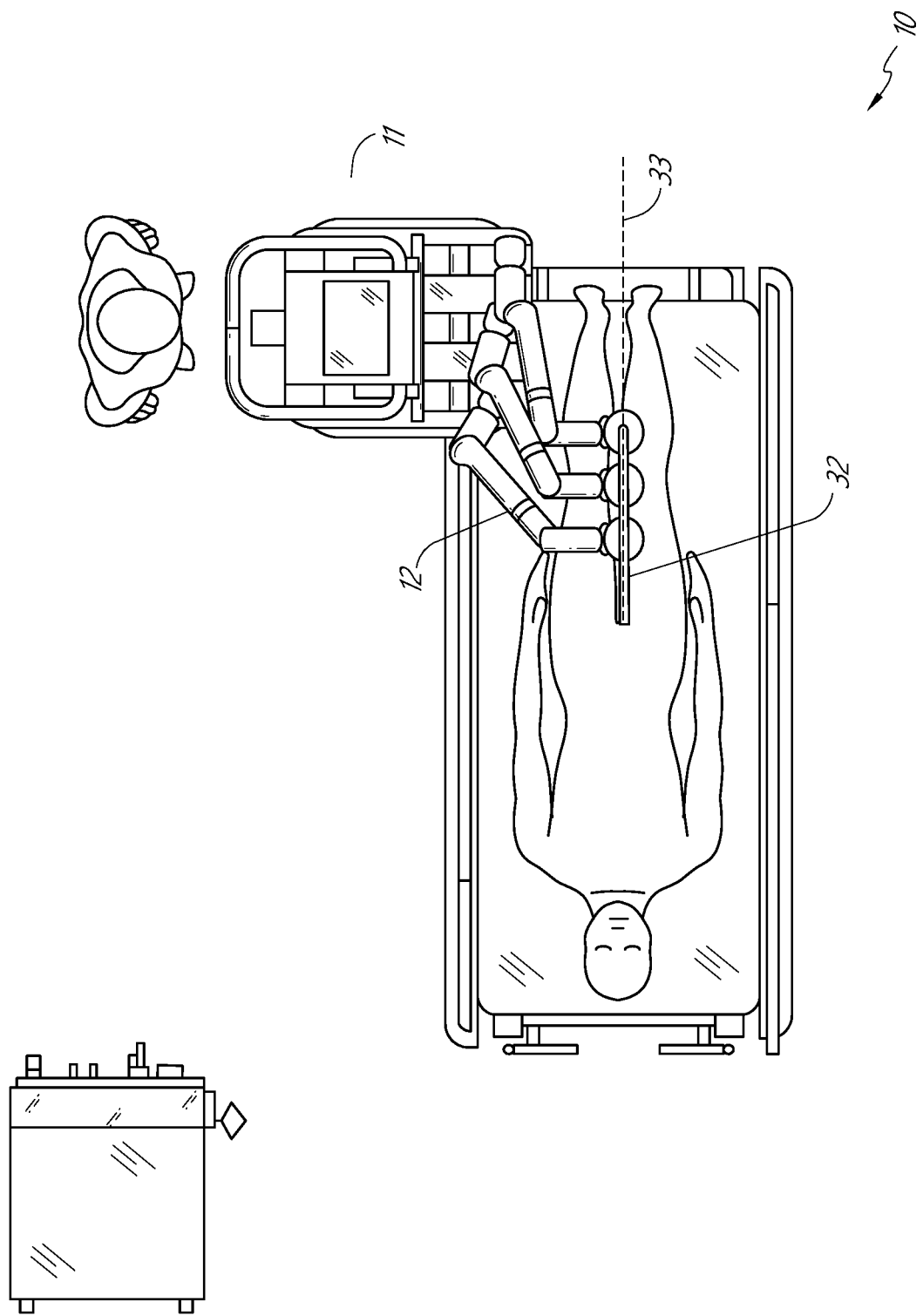
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
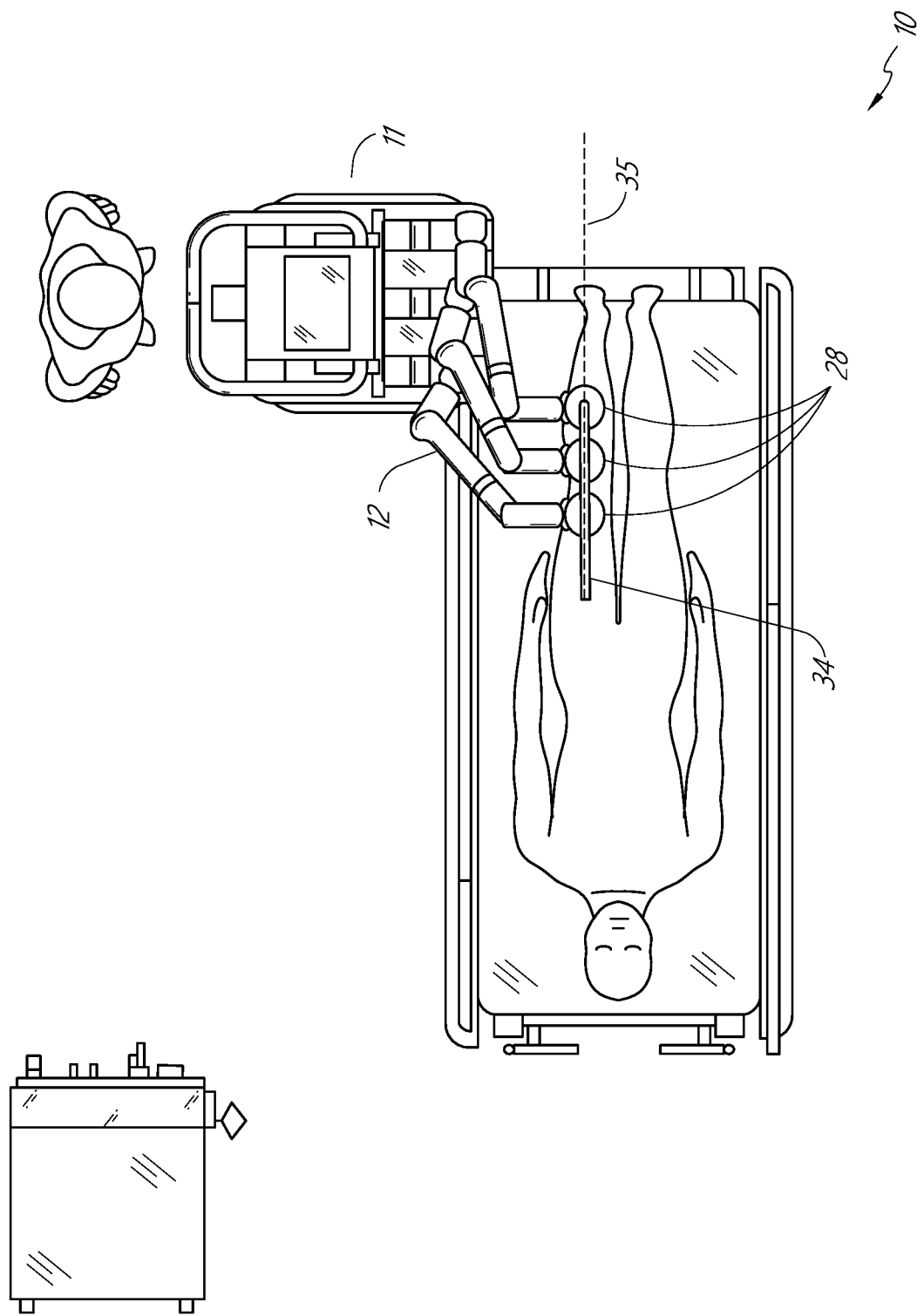
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
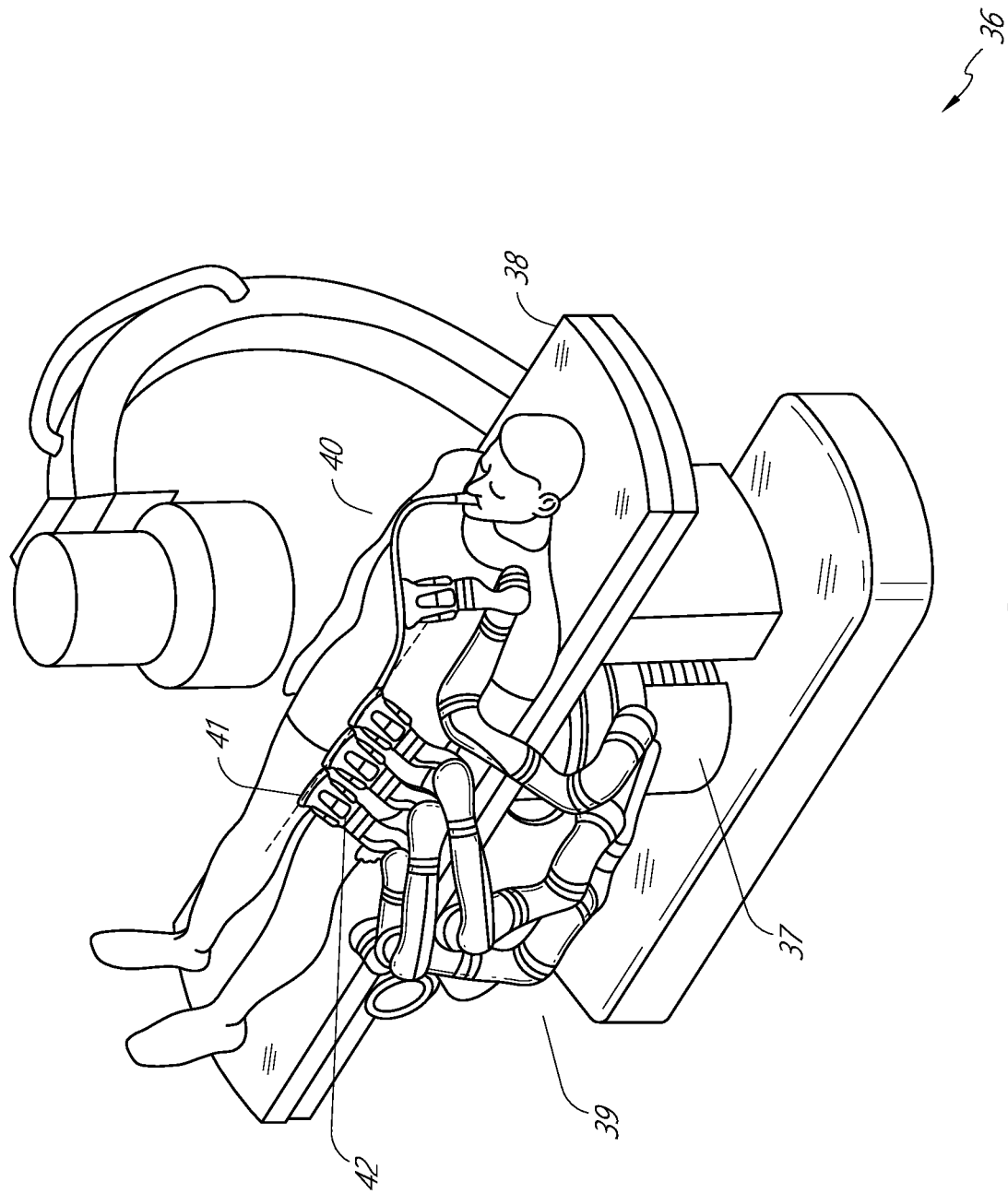
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
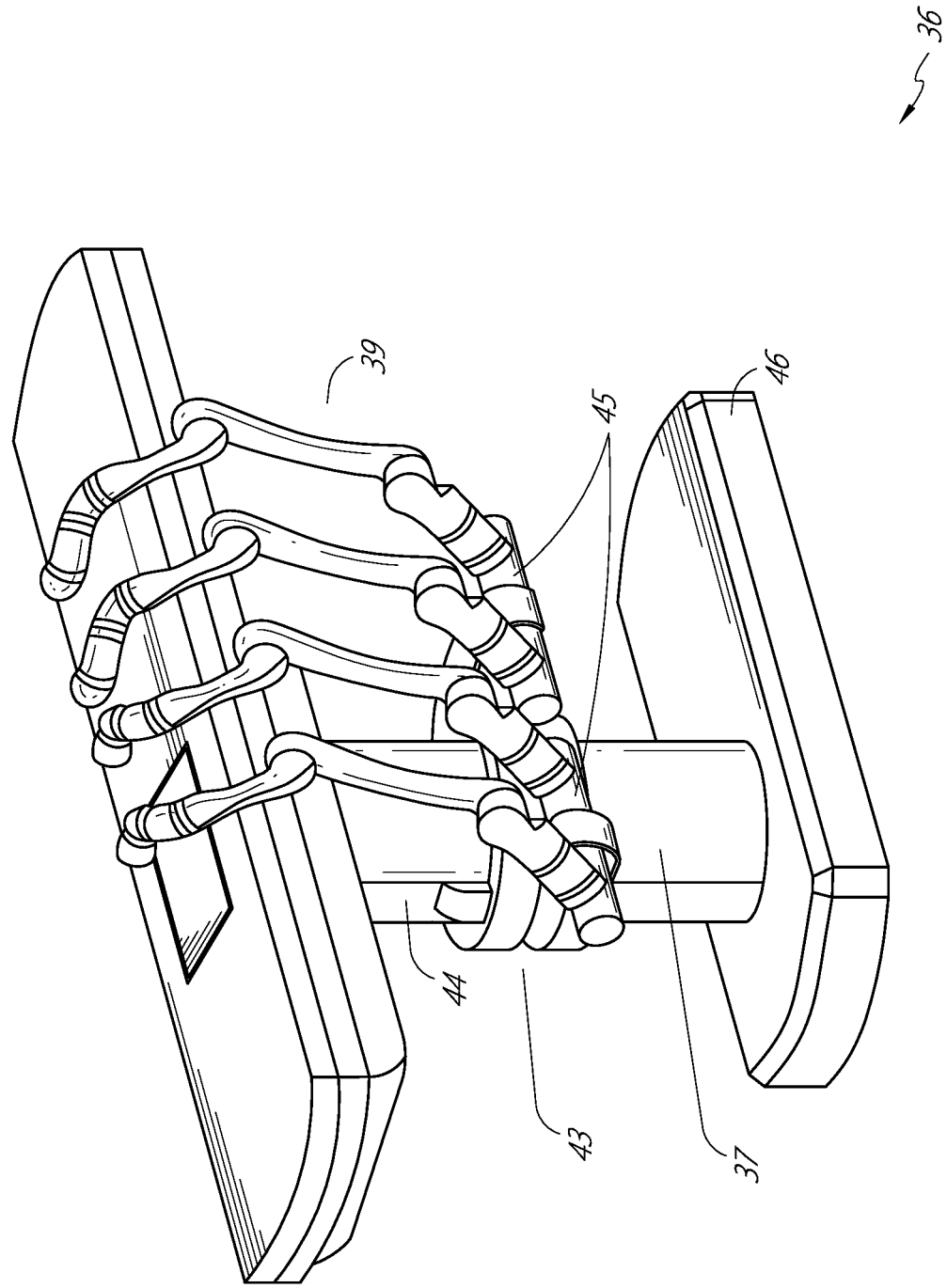
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
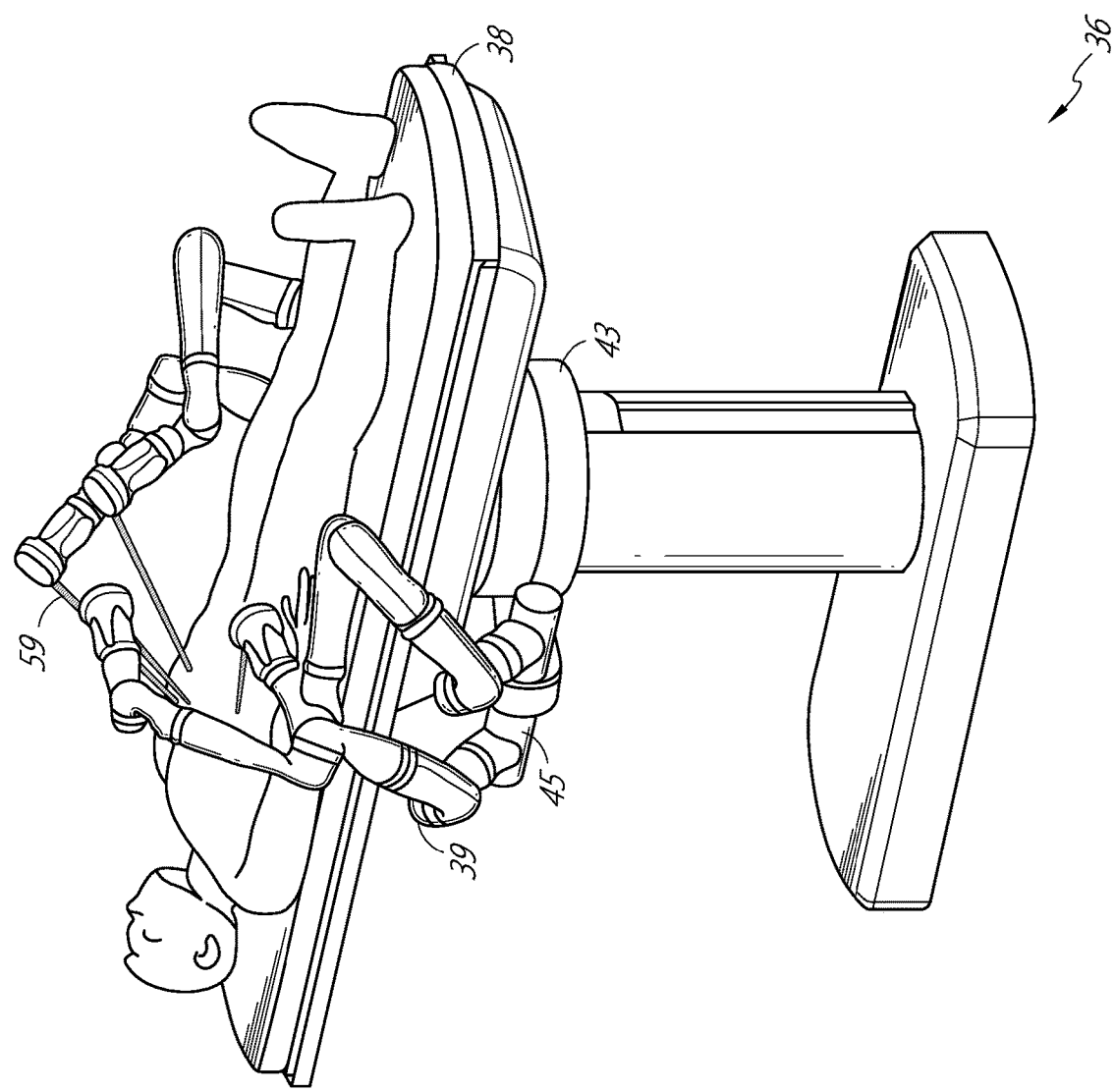
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may be provide a variety of support functionalities to table, such as processing, computing, and control capabilities, power, fluidics, and/or optical and sensor processing. The tower may also movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
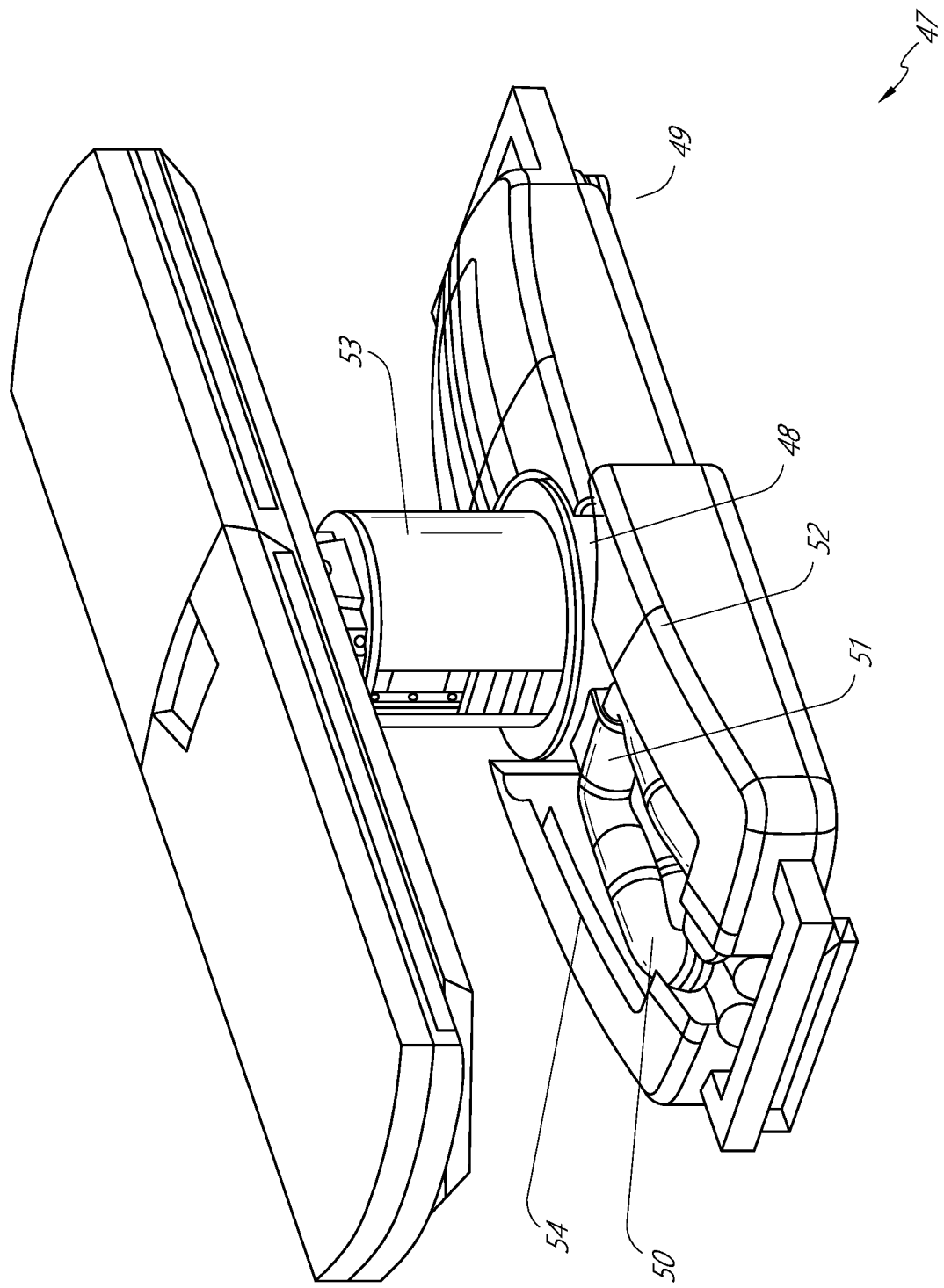
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
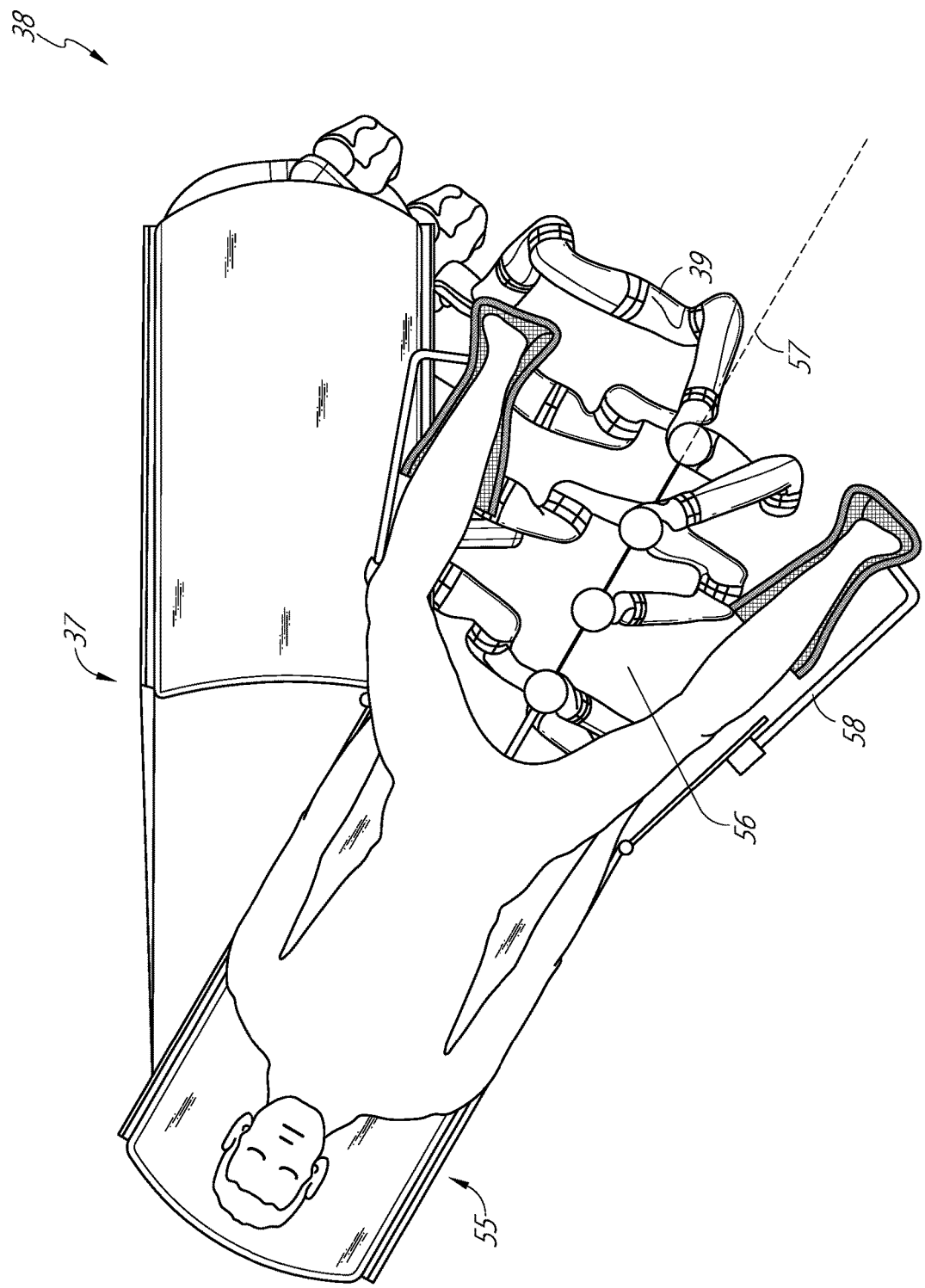
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instruments (e.g., laparoscopes) 59 may be positioned using the arm mounts 45 to be passed through minimal incisions on both sides of the patient to reach his/her abdominal cavity.

Figure 10:
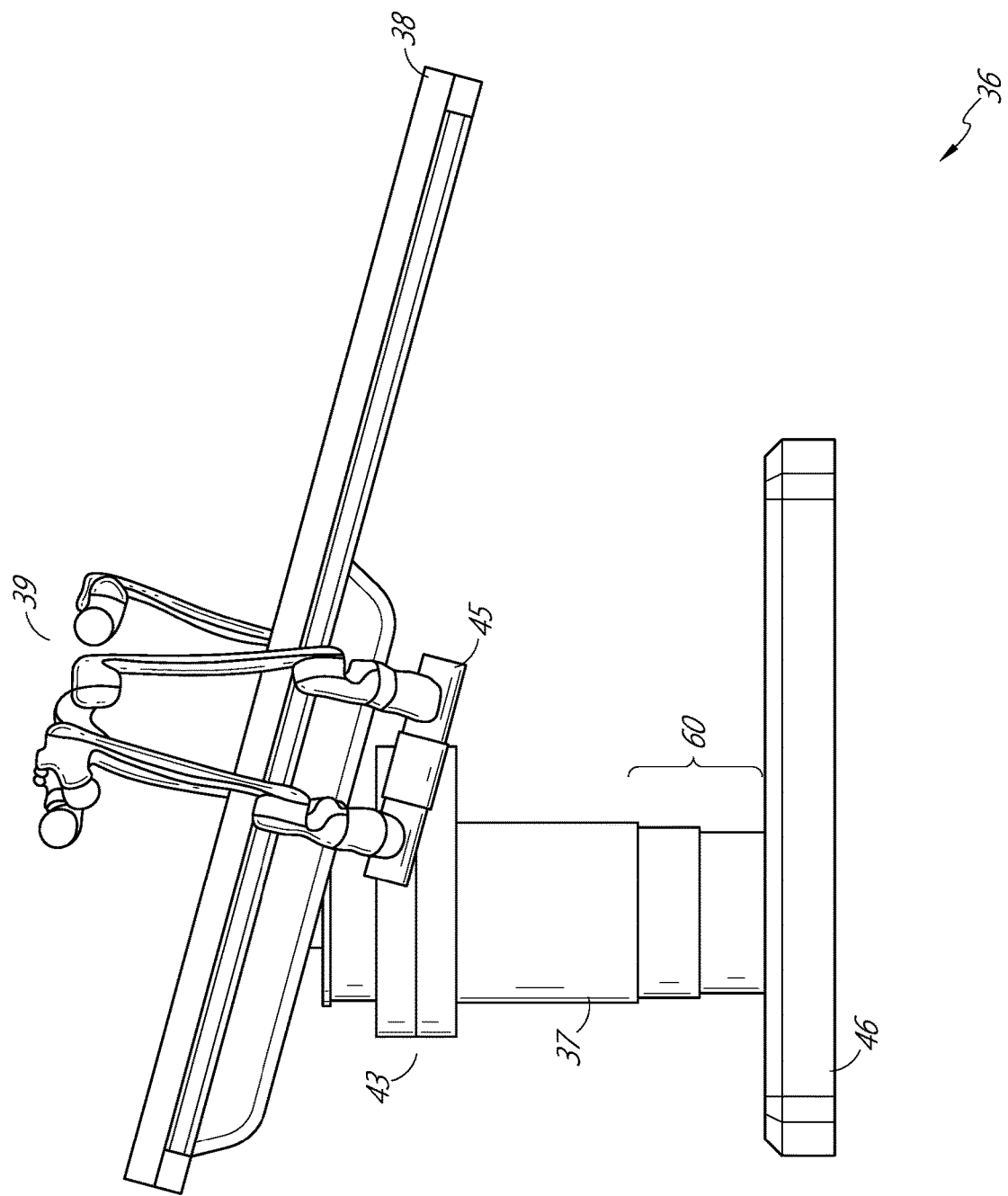
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
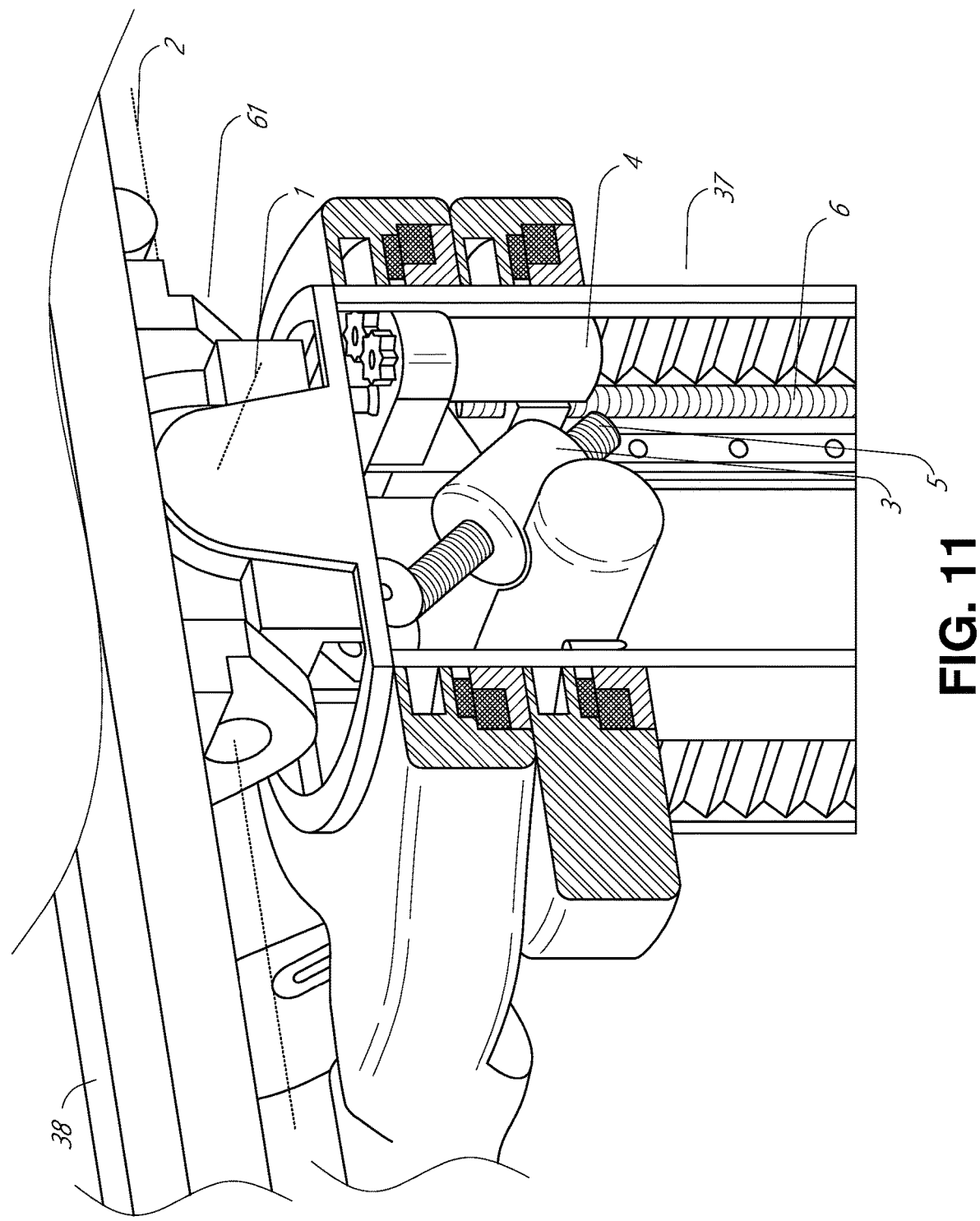
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator" (IDM)) that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
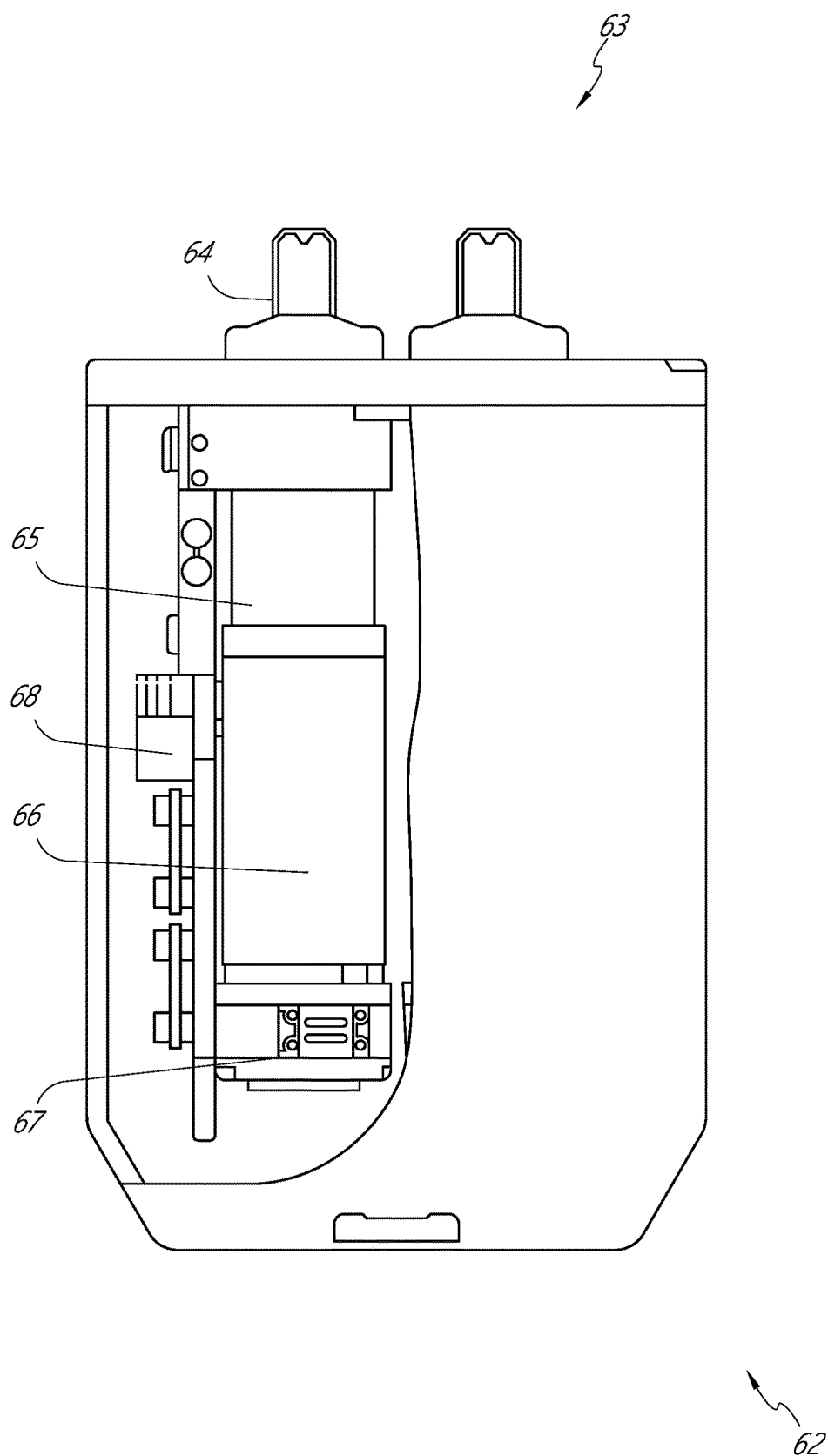
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
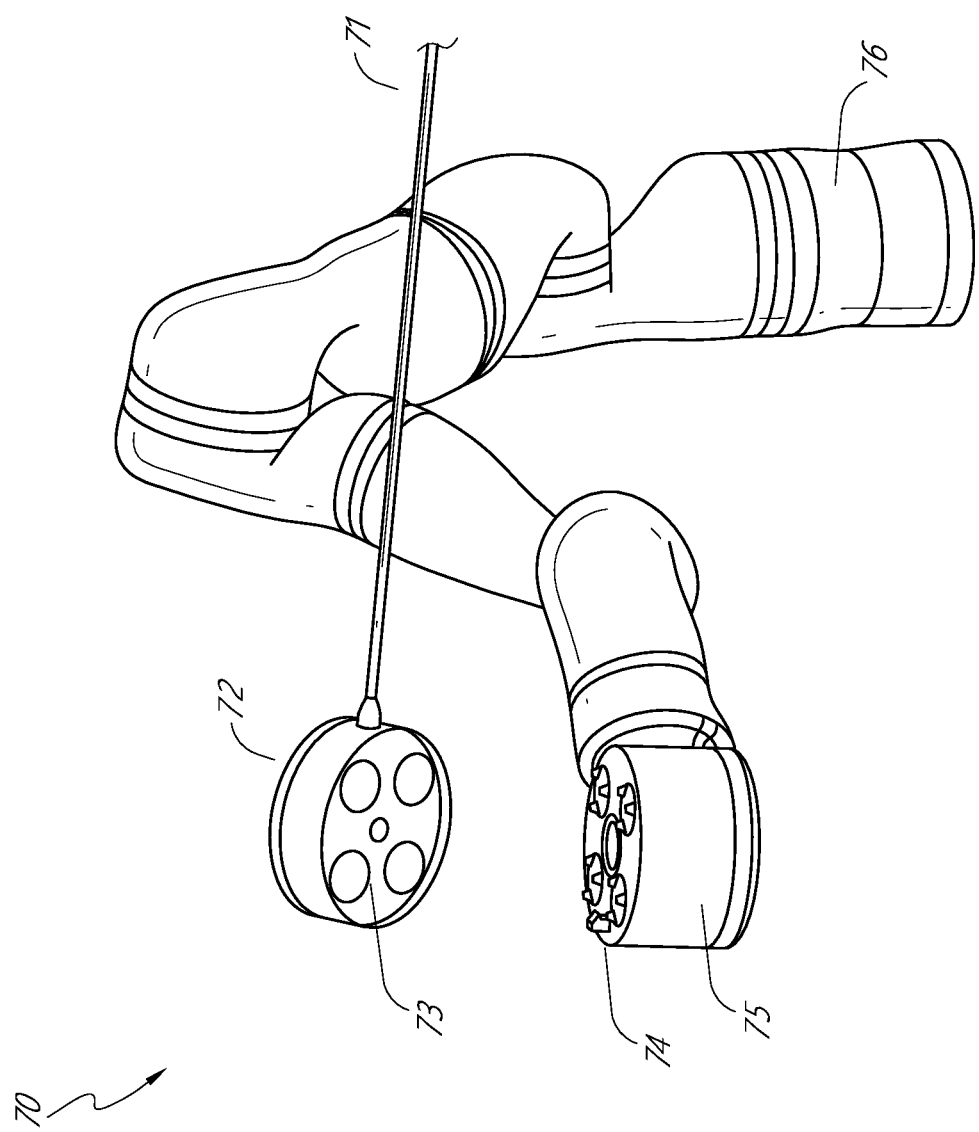
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at a distal portion of the elongated shaft. During a procedure, such as a laparoscopic, endoscopic, or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 14:
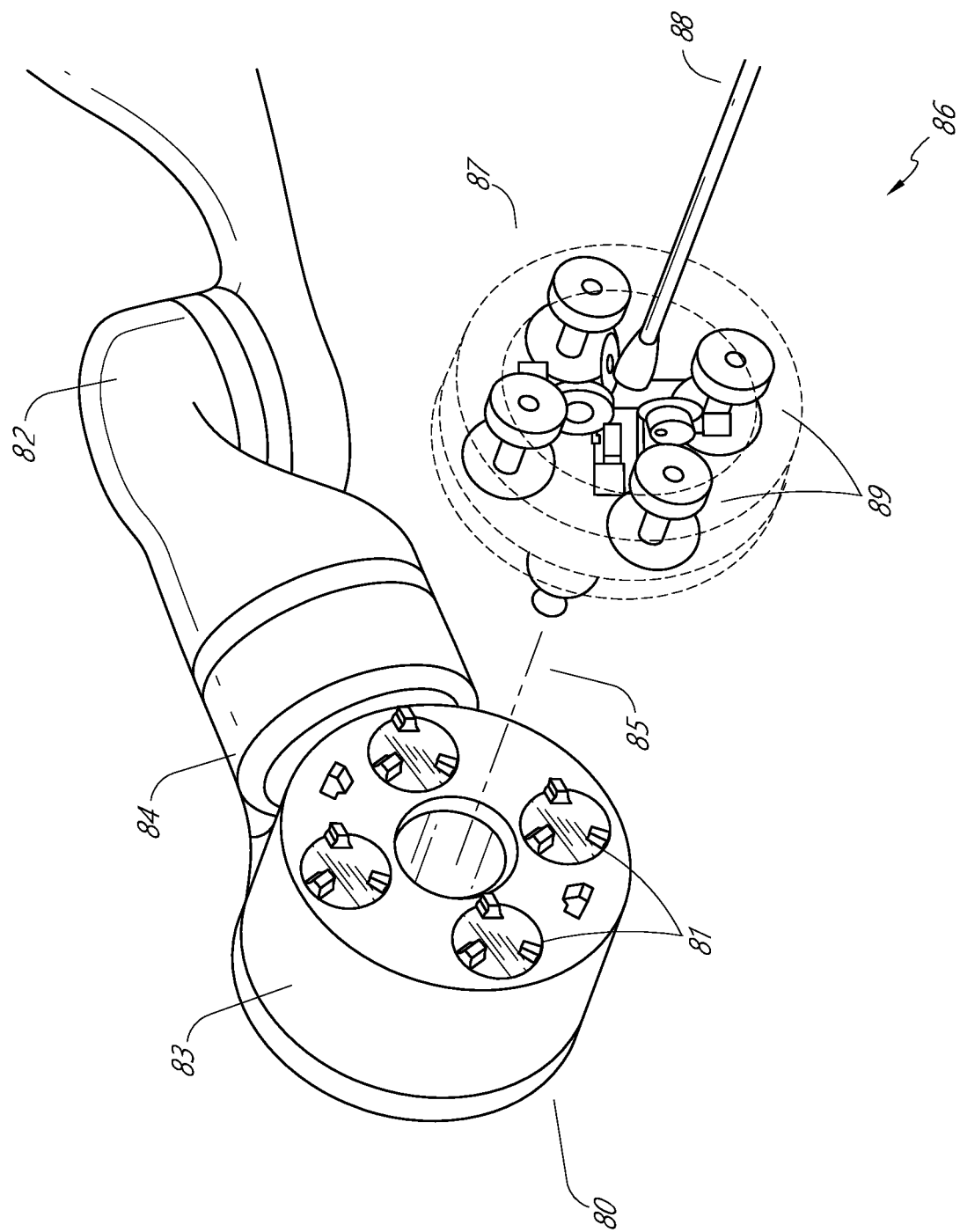
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
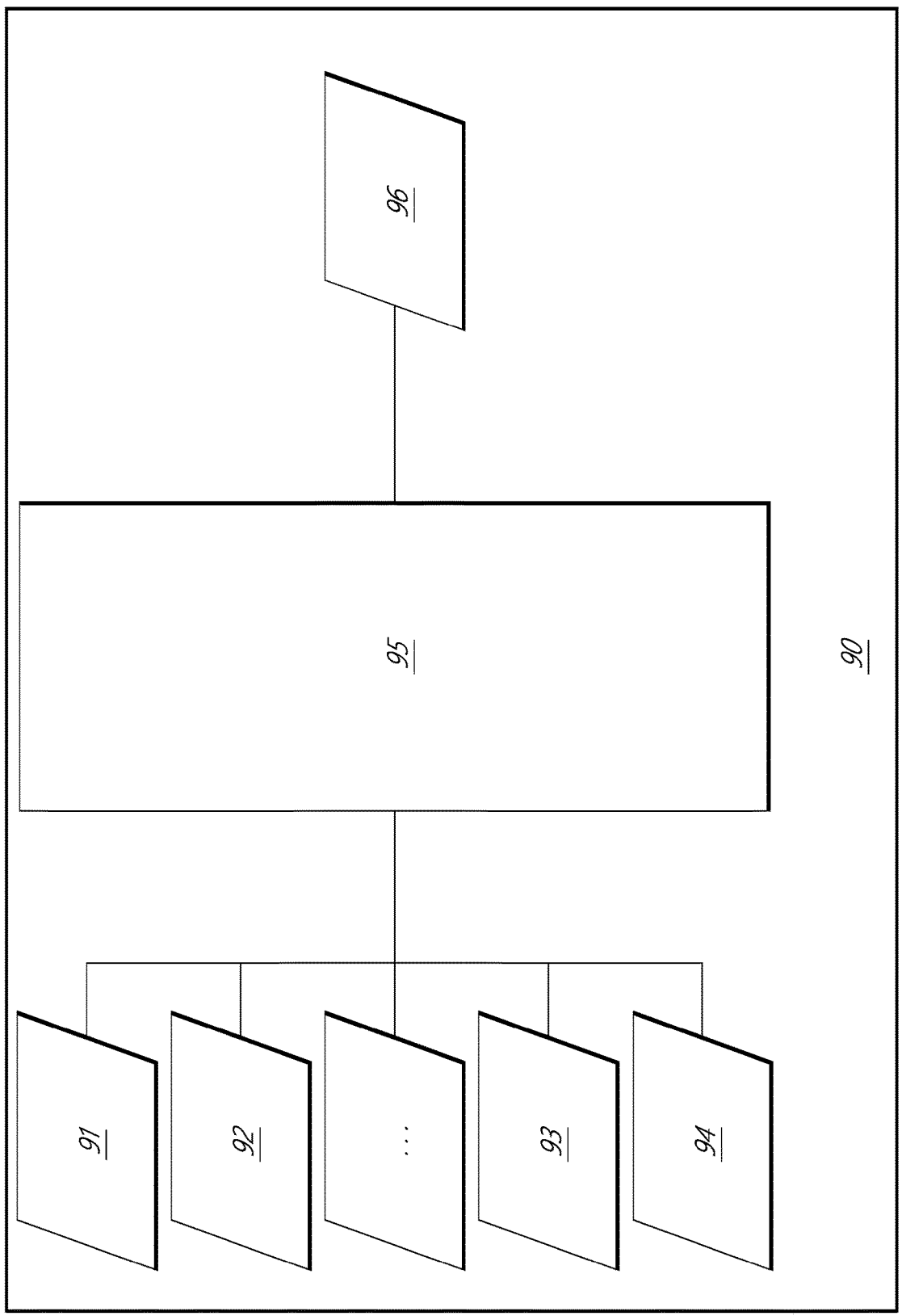
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Pre-Procedure Robotic Arm Setup.

Embodiments of the disclosure relate to systems and techniques for the positioning of one or more robotic arms prior to performing a medical procedure. Depending on the type of medical procedure, there may be limitations to the extent to which a robotic arm may be positioned or moved during setup of a surgical system. For example, certain physical or mechanical considerations, such as the shape and dimensions (e.g., length) of the medical instrument, the shape and physiological characteristics of the patient's luminal network, the location of a target destination for the procedure, the working area of the robotic arm(s), etc., may limit the area or volume in which the robotic arm(s) may be positioned during setup.

Setup procedures for surgical robotic systems may aid in ensuring and/or verifying that a given procedure is achievable. For example, a target destination or operative site may be located at a certain distance from an access point in the patient's body. Further, the length of the medical instrument and the stroke length of the robotic arm may be substantially fixed for a given surgical robotic system (e.g., robotic arm stroke length and medical instrument length may be standardized). As used herein, the stroke length of a robotic arm generally refers to the ability or extent to which the robotic arm can insert an instrument towards a target, such as, for example, from a starting position/location of a reference point of the robotic arm to an end position/location of the reference point. In one embodiment, the reference point may be the IDM of the robotic arm, and the stroke length may refer to the distance from a position of the IDM in the initial pose of the robotic arm for beginning the medical procedure (e.g., the initial pose and position of the robotic arm that facilitates the loading/attachment of instruments to the robotic arm, referred to herein as the load instruments pose) to a position of the IDM during maximum insertion of a medical instrument. For example, the stroke length of a robotic arm may determine whether the robotic arm is able to reach a target site/area from a given access point on the patient's body. Depending on the context, the "stroke length of the robotic arm" may also be used interchangeably with the "stroke length of a medical instrument" since the movement of the robotic arm may be directly correlated with the insertion/retraction of the medical instrument.

Given the length of the medical instrument, the distance from the access point to the target destination, and the maximum achievable stroke length of the robotic arm, there is a limit to the locations that may be used as the initial pose of the robotic arm prior to the surgical procedure. That is, certain initial poses of the robotic arm(s) will allow the medical instrument to reach the target destination while other initial poses may not enable the target destination to be reached. The placement of the cart with respect to the patient's access point, and thus, the location of the area/volume in which the robotic arm(s) can be freely positioned, may affect the achievable stroke length of the robotic arm(s). If the achievable stroke length is reduced to a length that is less than the distance from the access point to the target destination for a given medical procedure, the medical procedure may not be able to be performed based on the setup of the robotic system.

Aspects of this disclosure may relate to systems and techniques that aid a user (e.g., a technician or surgeon) in determining whether the desired procedure can be completed based on a given initial pose of the robotic arm. Such techniques may solve the problems associated with being unable to reach a target destination during a procedure.

A. Bronchoscopy System Example.

Aspects of this disclosure will be generally described using bronchoscopy as an exemplary medical procedure. However, this disclosure is also applicable to other types of medical procedures performed by a surgical robotic system, such as, for example, ureteroscopy, gastroenterology, etc.

Figure 16:
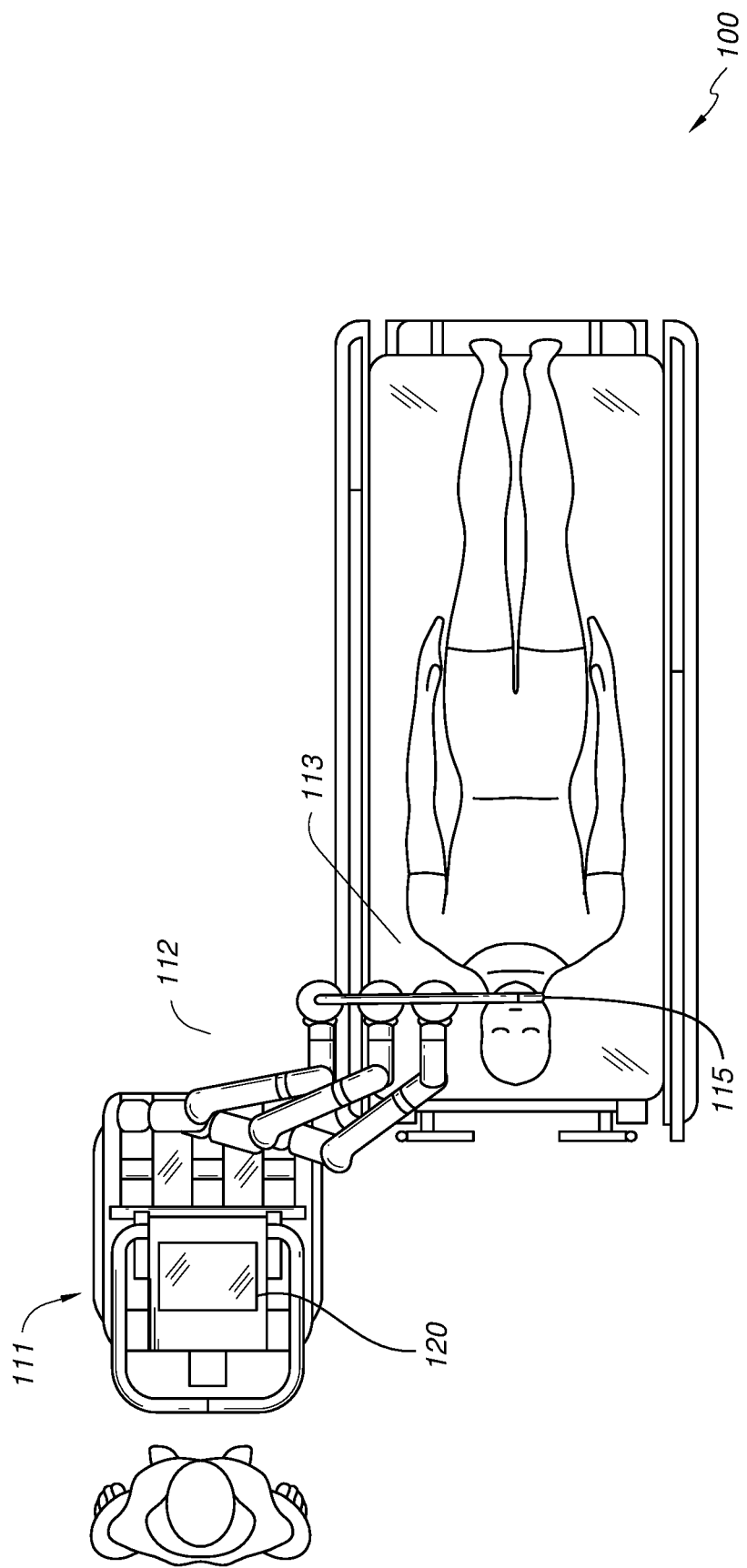
FIG. 16 illustrates an embodiment of a surgical robotic system arranged for diagnostic and/or therapeutic bronchoscopy procedure(s) in accordance with aspects of this disclosure.

FIG. 16 illustrates an embodiment of a robotic system arranged for diagnostic and/or therapeutic bronchoscopy procedure(s) in accordance with aspects of this disclosure. As shown in FIG. 16, the system 100 may include a cart 111, one or more robotic arm(s) 112, a medical instrument, such as a steerable endoscope 113, and a patient introducer 115. The cart 111 may include a processor (not illustrated), a memory (not illustrated), and a display 120 configured to display information related to the positioning of the robotic arm(s) 112. However, depending on the embodiment, one or more of the processor, the memory, and the display may be located on or within another device, such as, e.g., on the moveable tower 30 illustrated in FIG. 1. Additionally, in other implementations, a feedback device other than the display 120 may be used in place of, or in addition to, the display 120. Other feedback devices which may be employed include haptic devices, speakers, force-feedback actuated via one or more of the robotic arm(s) 112, one or more light-emitting diode(s), etc.

The robotic arm(s) 112 may be configured to manipulate the medical instrument (e.g., the steerable endoscope 113) prior to and/or during the procedure. During an arm setup phase (e.g., prior to beginning the medical procedure), the position of the robotic arm(s) 112 may be adjustable by the user. In particular, it may be important for at least one of the robotic arm(s) to be aligned with the patient. This alignment may enable the system to track the entry/access point of the medical instrument into the patient. Depending on the implementation, the system may be configured to allow the user to directly move the arm(s) 112 by applying a force directly to a portion of the robotic arm 112. For example, the system may be configured to detect when a user grabs one of the robotic arm(s) 112 and physically moves the arm 112 into a desired position by applying a force (e.g., pushing or pulling on the arm) to move the arm 112. In certain implementations, the system may accept input from a user to toggle the arm into and out of an admittance mode in which the arm accepts force as input for movement of the arm. In other implementations, the system may include an input device configured to enable the user to adjust the position of one or more of the robotic arm(s) via the input device for the control of the robotic arms 112.

As will be described in greater detail below, the memory may be configured to store instructions, that when executed, cause the processor to perform one or more techniques in accordance with aspects of this disclosure. The memory may be further configured to store data relevant to the pre-procedure robotic arm setup. For example, the memory may store a mapping of an anatomy of a patient. The mapping may comprise data regarding (i) a target region within the anatomy and (ii) a path from an access point of the patient to the target region. The mapping may comprise or be based on procedure data related to the medical procedure being performed. The procedure data may include data regarding: the type of procedure being performed, the type of instrument involved in the procedure (which may relate to the type of the procedure), attributes of the instrument (e.g., the length of the instrument, the number of IDMs required for manipulating the instrument, etc.), the patient's anatomy relevant to the procedure (e.g., the location of a target region within the anatomy, a path from an access point of the patient to the target region, physiological characteristics or dimensions of the patient's anatomy, etc.), the arm setup (which may also relate to the type of the procedure, the type of the instrument, and the attributes of the instrument), etc. For example, the mapping may include the location of the target region within the anatomy and the path from the access point of the patient to the target region, which may be determined based on the procedure data.

B. Robotic Arm Setup.

Positioning of one or more of the robotic arm(s) 112 may be one part of a setup procedure for preparing the robotic arm system for a medical procedure. The specific setup procedure used may depend on the medical procedure being performed, the configuration of the robotic system (e.g., whether the arms are attached to a cart (see FIG. 16) or attached to a column supporting the platform (see FIG. 6)), etc.

Figure 17A:
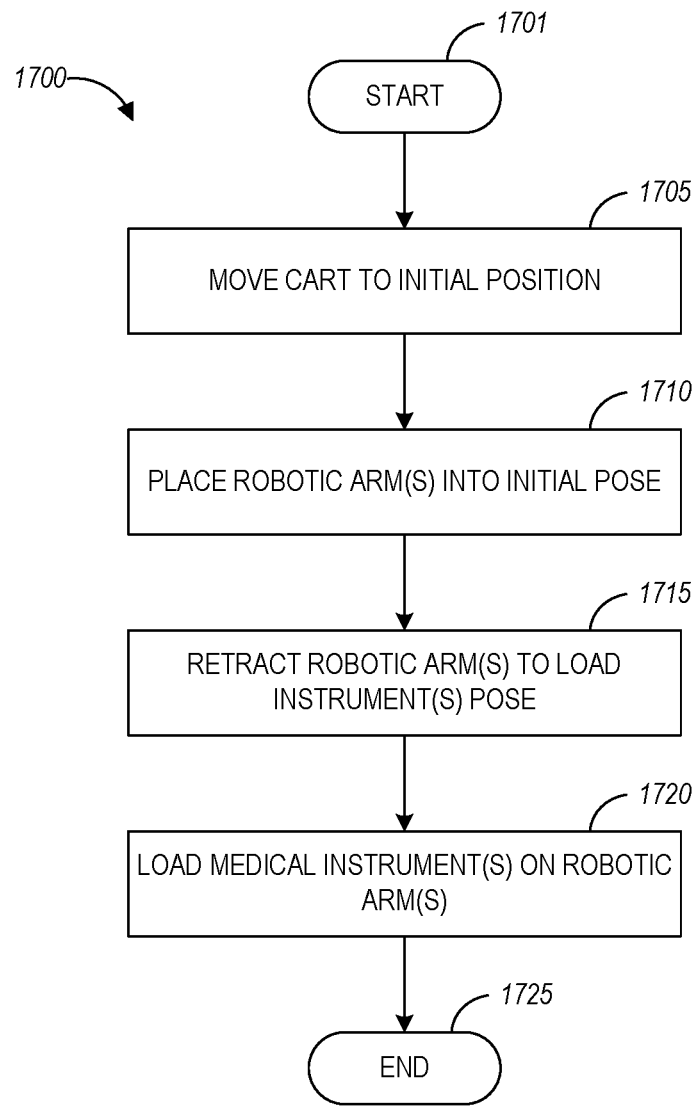
FIG. 17A is a flow-chart which illustrates features of an example setup procedure for a medical procedure in accordance with aspects of this disclosure.

FIG. 17A is a flow-chart which illustrates features of an example setup procedure for a medical procedure (e.g., bronchoscopy) in accordance with aspects of this disclosure. The method 1700 illustrated in FIG. 17A is merely an example implementation and the method 1700 may be modified by adding, removing, and or modifying one or more of the blocks associated with the method 1700.

The method 1700 begins at block 1701. At block 1705, the method 1700 involves moving the cart to an initial position. For example, a user may move the cart to be positioned proximate to (e.g., within a defined distance of) the patient's access point. Once the cart has been moved into position, the user may immobilize the cart by, for example, locking the casters of the cart. It is to be appreciated that not all robotic systems may utilize a cart and this block is optional for those systems that do utilize a cart.

Block 1710 may involve an arm setup phase, in which the user may place one or more of the robotic arm(s) into an initial pose where the robotic arm(s) are aligned with the patient prior to performing the procedure. Thus, the arm setup phase may include an alignment step for aligning one or more of the robotic arm(s) 112 with an access point of the patient. Since the access point used may depend on the type of the medical procedure being performed, the specific alignment procedure may depend on the medical procedure type. In the bronchoscopy example, a patient introducer (a device which guides the bronchoscope into the patient's mouth) may be installed into the patient's mouth. In one implementation of a bronchoscopy setup procedure, the user may align a first one of the robotic arms with the patient introducer. The remaining robotic arm(s) may, e.g., automatically align with the pose of the first robotic arm selected by the user. As described above, the user may be able to directly move the robotic arm by pressing an admittance button which allows the user to direct movement of the robotic arm by applying force(s) thereto. In other implementations, the first robotic arm may track the patient introducer via one or more position tracking devices, enabling the first robotic arm to be automatically aligned with the patient introducer by the system.

The system may provide an indication of a boundary for an initial pose of the first robotic arm to the user. In certain embodiments, the system may, during an arm setup phase prior to performing a medical procedure, provide the indication of the boundary during movement of the first robotic arm. The boundary may be set by the system to ensure that the pose of the first robotic arm does not interfere with the medical procedure. In one implementation, the boundary may be set as an area or volume in which the first robotic arm can be freely positioned without reducing the stroke length of the robotic arm by more than a threshold amount. In a bronchoscopy example, the boundary may define an area in which the robotic arm may be aligned with the patient introducer such that the distance between the initial pose of the robotic arm (e.g., the pose of the robotic arm in alignment with the patient introducer) and the load instruments pose is equal to or greater than a threshold stroke length. In certain embodiments, the threshold stroke length may be selected such that a target region associated with the medical procedure can be reached when the stroke length achievable by the robotic arm is greater than the threshold stroke length.

After the first robotic arm is aligned with the patient introducer, at block 1715, the method involves retracting the robotic arm(s) into a load instrument(s) pose. In some embodiments, the system may retract the robotic arm(s) into the load instrument(s) pose in response to receiving a load-instrument-pose input or command e.g., from the user. This input may indicate that the alignment step has been completed and that instrument(s) (e.g., the sheath and leader of the bronchoscope) are to be loaded onto the robotic arm(s). At block 1720, the method involves loading the medical instrument(s) onto the corresponding robotic arm(s). The method 1700 ends at block 1725.

Figure 17B:
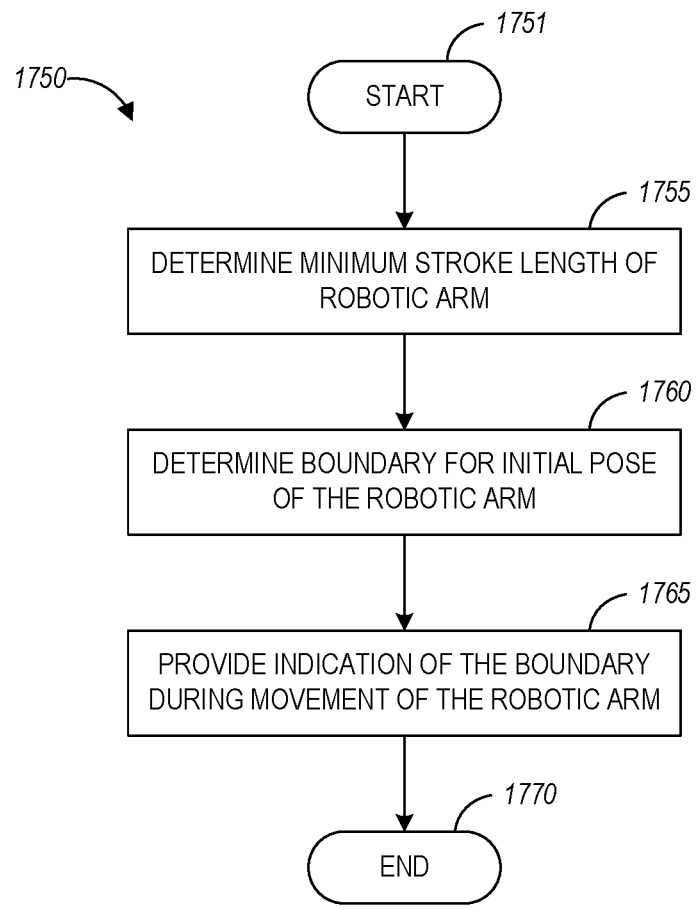
FIG. 17B is a flow-chart which illustrates features of another example setup procedure for a medical procedure in accordance with aspects of this disclosure.

FIG. 17B is a flowchart which illustrates features of another example setup procedure for a medical procedure in accordance with aspects of this disclosure. The flowchart of FIG. 17B illustrates an example method operable by a surgical robotic system, or component(s) thereof, for positioning one or more robotic arms prior to performing a medical procedure in accordance with aspects of this disclosure. For example, the steps of method 1750 illustrated in FIG. 17B may be performed by a processor of a surgical robotic system. For convenience, the method 1750 is described as performed by the processor of the system.

The method 1750 may be performed as a part of a setup procedure for a medical procedure, such as the medical procedure 1700 illustrated in FIG. 17A. In certain implementations, the method 1750 may be performed during block 1710 to provide an indication of a boundary during movement of a robotic arm.

The method 1750 begins at block 1751. At block 1755 the processor determines a minimum stroke length of the robotic arm that allows advancing of a medical instrument by the robotic arm to reach a target region. The processor may determine the minimum stroke length based on a mapping of an anatomy of a patient. The mapping may comprise data regarding (i) the target region within the anatomy and (ii) a path from an access point of the patient to the target region. The medical instrument may be advanced by the robotic arm to reach the target region from the access point via the path.

At block 1760, the processor determines a boundary for an initial pose of the robotic arm based on the minimum stroke length and the mapping. At block 1765, the processor, during an arm setup phase prior to performing a procedure, provides an indication of the boundary during movement of the robotic arm. The method 1750 ends at block 1770.

Since the structure of the medical instrument and the robotic arms are known prior to performing the medical procedure, the boundary can be determined offline (e.g., prior to the arm setup phase). However, depending on the complexity of the medical procedure and the medical instrument, the determination of the boundary may require a significant amount of computational resources. In certain cases, the computation may take on the order of hours to complete. An example of the considerations for defining the initial pose boundary will be described in connection with FIG. 18.

Figure 18:
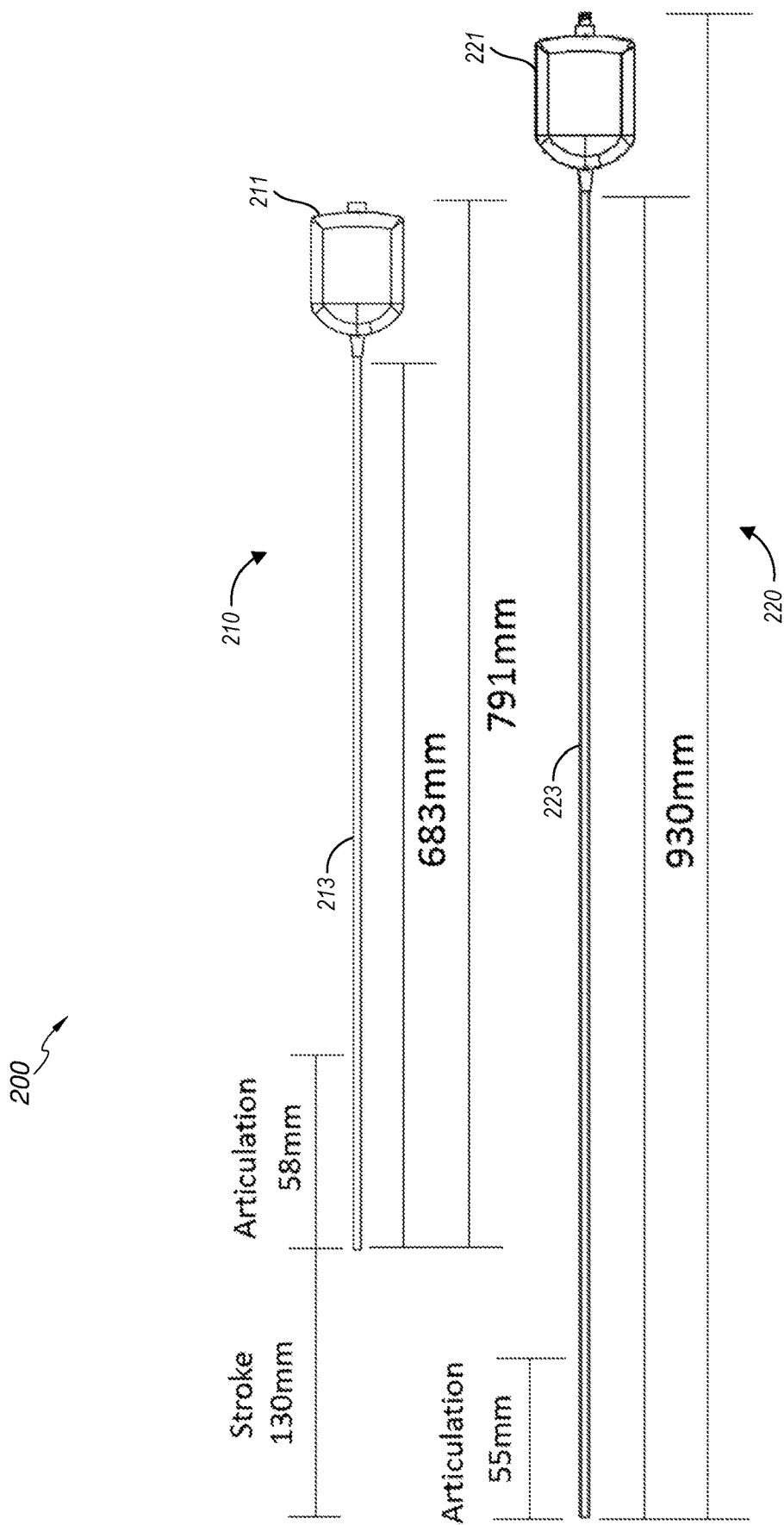
FIG. 18 illustrates an embodiment of a bronchoscope which may be used in accordance with aspects of this disclosure.

FIG. 18 illustrates an embodiment of a bronchoscope which may be used in accordance with aspects of this disclosure. As shown in FIG. 18, the bronchoscope 200 may include two telescoping parts—namely, a sheath 210 and a leader 220. For example, the leader 220 may be the part that comprises the camera/vision device, the EM sensors, and the working channel through which other instruments can be inserted. The sheath 210 may include a base 211, configured to be coupled to an IDM of a first robotic arm, and an elongated shaft 213 attached to the base 211. Similarly, the leader 220 may include a base 221, configured to be coupled to an IDM of a second robotic arm, and an elongated shaft 223 attached to the base 221. The first and the second robotic arms may be configured to advance the sheath 210 and the leader 220, respectively. The elongated shaft 213 of the sheath 210 comprises a working channel through which the elongated shaft 223 of the leader 220 is configured to be inserted. Each of the distal ends of each of the elongated shafts 213 and 223 may comprise an articulating section configured to be bent via tension applied to tendons arranged along (or inside) the walls of the corresponding elongated shafts.

In the example illustrated in FIG. 18, the elongated shaft 213 of the sheath 210 has a length of about 683 mm. As such, the maximum stroke length of the elongated shaft 213 is about 683 mm minus the working length of the patient introducer. If the working length of the patient introducer is about 150 mm, just as an example and not a limitation, the maximum stroke length of the elongated shaft 213 of the sheath 210 may be about 533 mm. Further, the elongated shaft 223 of the leader 220 may be about 930 mm in this example. Here, the leader 220 may be extended about 130 mm past the distal end of the sheath 210 to allow the distal end of the leader 220 to access the target site, e.g., to perform a medical procedure. Accordingly, the maximum stroke length of the leader 220 may be about 663 mm in one example.

However, the respective maximum stroke lengths of the sheath 210 and leader 220 may be reduced based on the setup positioning of the cart and robotic arms. For example, if the first robotic arm (e.g., the arm attached to the sheath 210) reaches its maximum extension prior to contacting the patient introducer, the first robotic arm will not able to further insert the sheath 210, reducing the achievable stroke length. In another example, after aligning the first robotic arm with the patient introducer at an initial pose (e.g., in a partially extended pose), the first robotic arm is retracted to a load instruments pose. However, the distance between the load instruments pose and the initial pose may not be sufficient to achieve the full insertion of the sheath 210. Similar considerations affect the achievable stroke length of the leader 220.

Another factor which may limit the achievable stroke length of the sheath 210 and/or the leader 220 include potential collisions between one or more of the robotic arm(s) and other objects present in the operating environment. For example, if the IDM of the second robotic arm (attached to the leader) is prevented from moving into contact with the IDM of the first robotic arm, the leader 220 will lose a portion of the stroke length of the leader 220 past the distal end of the sheath 210.

Figure 19:
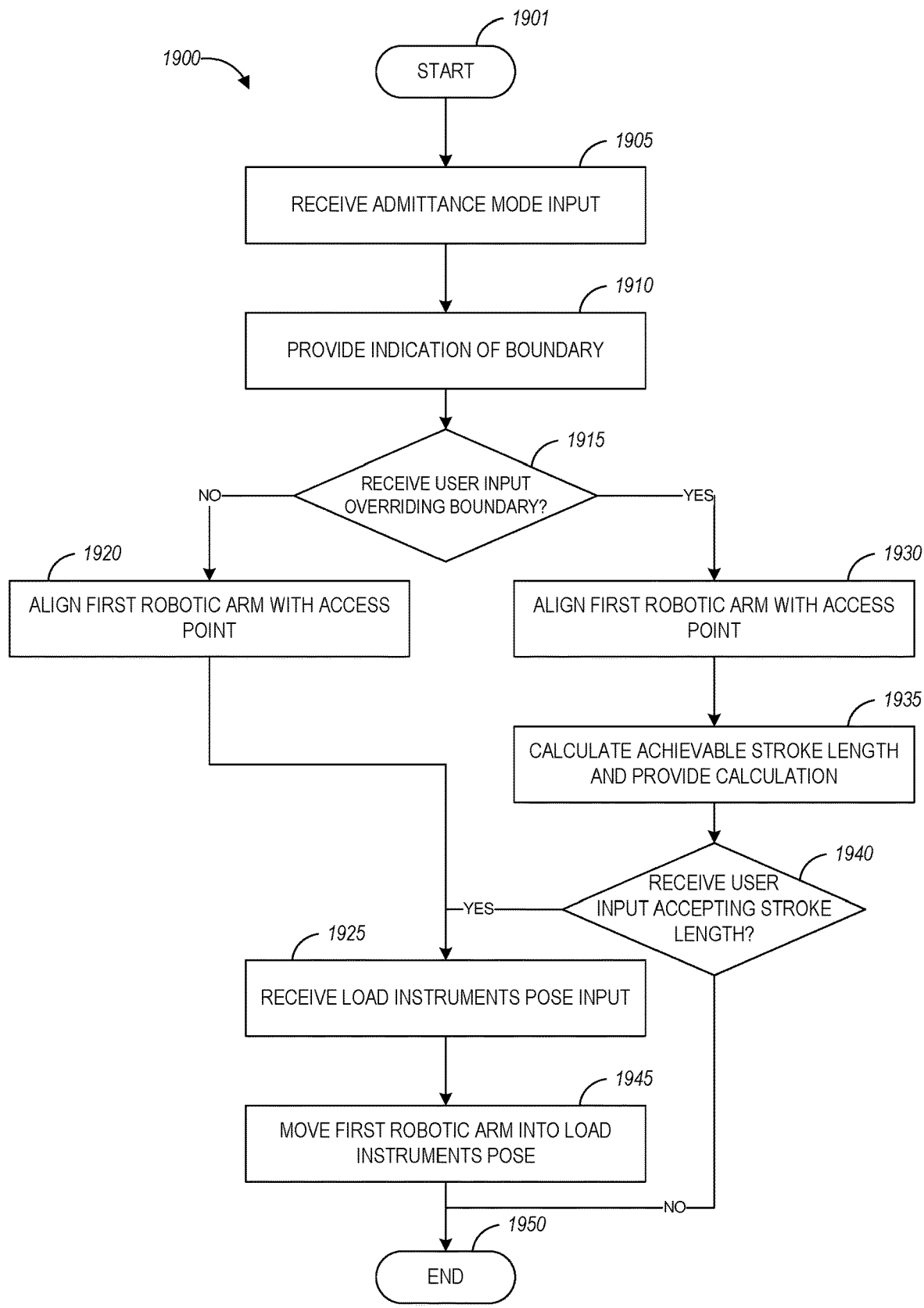
FIG. 19 is a flow-chart which illustrates another example of a setup procedure for a bronchoscopy procedure in accordance with aspects of this disclosure.

FIG. 19 is a flow-chart which illustrates another example of a setup procedure for a bronchoscopy procedure in accordance with aspects of this disclosure. The method 1900 may begin after a user has positioned a cart adjacent to a patient for alignment of one or more robotic arms of the cart with the patient. The method 1900 begins at block 1901. At block 1905, the system receives an admittance mode input from a user. One of robotic arms may include an admittance button (e.g., on or near the IDM) to allow the user to transition into admittance mode. As described above, admittance mode may allow the user to apply a force directly to a portion of the robotic arm as input for moving the arm. In certain implementations, each of the robotic arms may maintain a substantially constant separation and relative orientation as the user moves a first robotic arm (of the one or more robotic arms) in admittance mode.

At block 1910, the system provides an indication of a boundary to the user. The boundary may be an area in which the user is permitted to move the first robotic arm in the admittance mode. The boundary may be determined by the system such that when the first robotic arm is aligned with the an access point within the boundary, the stroke lengths of each of the sheath and the leader are above a predetermined threshold (also referred to as "stroke length threshold" herein). In one example, the access point may comprise a patient introducer which may be installed, e.g., in the user's mouth when performing a bronchoscopy procedure. However, in other medical procedures, the access point may comprise another device designed to guide the medical instrument into the user via the access point. The access point may also be a natural orifice (e.g., the patient's mouth) without a device installed therein. In other embodiments, the access point may be small incision(s) which allow instrument(s) to access the patient's anatomy in a minimally invasive manner.

Depending on the embodiment, the system may provide the indication of the boundary via at least one of: a haptic indication, a visual indication, and an audio indication. For example, the system may provide a visual indication of the position of the first robotic arm within a boundary via a display to the user. In another embodiment, a speaker may be used to indicate the distance to the closest portion of the boundary or may provide an indication that the user has moved the first robotic arm within a threshold distance of the boundary to provide a warning that that the first robotic arm is approaching the boundary.

In another embodiment, the system may provide a haptic indication of the boundary to the user. For example, the motors in the first robotic arm may freely allow the user to move the first robotic arm within the boundary, but may prevent movement of the first robotic arm outside of the boundary. In certain implementations, this may feel to the user like the IDM of the first robotic arm is hitting an invisible wall. Alternatively, the first robotic arm may increase a simulated resistance to movement as the first robotic arm approaches the boundary and prevent further movement once the IDM reaches the boundary. Accordingly, the system may limit the movement of the first robotic arm within the boundary area during the arm setup phase. In other embodiments, such as when the boundary is represented by a volume, the system may limit the movement of the first robotic arm within the boundary volume during the arm setup phase.

In certain embodiments, the boundary is a two-dimensional area and only limits movement within the plane of the boundary. For example, in a bronchoscopy embodiment, the vertical (Z-axis) of the IDM is aligned with a corresponding feature of the patient introducer. This height is generally fixed during the procedure and the insertion of the bronchoscope into the patient does not require any substantial movement in the Z-axis. Thus, changes in the Z-axis of the first robotic arm during the arm setup phase may not significantly affect the achievable stroke length. In these embodiments, the boundary can be thus be defined solely in the X-Y plane, allowing freedom of movement in the Z-axis.

However, other medical procedures and/or robotic system configurations may include movement of one or more robotic arms in the Z-axis during the medical procedure. In these embodiments, the boundary may be define in three dimensions including in the Z-axis.

Returning to the method 1900, at block 1915, the system may receive or detect an input from the user overriding the boundary previously provided to the user. For example, the cart may not have been placed in the ideal position prior to starting the arm setup phase, and thus, the access point (e.g., a patient introducer) may not be within the boundary. When the access point cannot be reached by the IDM of the first robotic arm, the user may wish to override the boundary to determine whether the first robotic arm can be aligned with the access point outside of the boundary. The user may override the boundary by inputting an override command to the system via, for example, an override input or another input/output device (e.g., a touchscreen display) coupled to the system.

In response to detecting an input to not override the boundary, at block 1920, the system aligns the first robotic arm with the access point based on input received from the user. For example, the user may apply a force to the first robotic arm in admittance mode and the system may alter the position of the first robotic arm using the force as an input. This alignment may involve matching a marking, or other alignment device, on the IDM of the first robotic arm with a corresponding marking or alignment device on the access point (e.g., the patient introducer). Examples of the alignment device include corresponding physical members on the IDM and patient introducer which can be mated together, electronic communication devices such as an RFID tag/reader, positional tracking systems (which may be based on optical and/or acoustic technology), etc. After the first robotic arm is aligned with the access point, at block 1925, the system receives a load instrument pose input from the user. This input may indicate that the user has completed the alignment step and is ready to load the instrument(s) (e.g., the sheath and leader of the bronchoscope) onto the robotic arm(s).

At block 1945, the system moves the first robotic arm to the load instruments pose so that a user may load a medical instrument onto the first robotic arm.

In response to detecting an input from the user to override the boundary, at block 1930, the system aligns the robotic arm with the access point based on input received from the user. For example, the user may apply a force to the first robotic arm in admittance mode and the system may alter the position of the first robotic arm using the force as an input. In this case, the user may move the first robotic arm outside of the boundary previously provided to the user in block 1910. At block 1935, the system calculates the achievable stroke length and provides an indication of the calculated result to the user. In one implementation, the system may calculate and provide the indication to the user in "real-time." For example, the system may detect the movement of the first robotic arm at a sampling frequency. The system may then determine a position of the first robotic arm based on the detected movement of the first robotic arm. The system may then simulate, based on the position of the first robotic arm, an achievable stroke length of the first robotic arm that facilitates advancing the medical instrument into the patient. One technique for simulating the achievable stroke length will be described in greater detail below in connection with FIG. 20.

There are a number of different techniques which may be used to provide the indication of the achievable stroke length to the user. In one implementation, the system may provide a numerical value to the user that is representative of the simulated achievable stroke length. In another implementation, the system may store (e.g., in memory) the required stroke length for performing a specific medical procedure on the patient. In certain embodiments, the required stroke length may be the minimum stroke length of the robotic arm that allows advancing of a medical instrument by the robotic arm to reach a target region from the patient's access point via a predetermined path therebetween.

For example, prior to the arm setup phase, an image of the patient's luminal network may have been captured. For certain medical procedures, a pre-operative mapping of the patient's luminal network may have been performed through the use of the collection of low dose CT scans. Based on the mapping, the system may determine a path from the selected access point to the target destination and calculate the stroke length required to reach the target destination via the determined path. The system may then compare the required stroke length to the achievable stroke length and provide an indication of whether the target destination can be reached to the user based on the pose of the first robotic arm. For example, the system may determine whether the achievable stroke length is greater than or equal to the minimum stroke length and provide an indication of whether the achievable stroke length is greater than or equal to the minimum stroke length. Depending on the computational bandwidth of the system, the system may be able to continually update the simulation of the procedure and provide the indication of whether the desired target destination can be reached as the user moves the first robotic arm in admittance mode.

In certain embodiment, the system may determine whether the achievable stroke length is greater than or equal to the minimum stroke length in response to the user releasing the admittance mode button. For example, while in admittance mode, the user may still be moving the robotic arm into alignment, and thus, the initial pose of the robotic arm may not be set while the admittance button is depressed. After the user has released the admittance button, the system may infer that the pose of the first robotic arm is in alignment with the access point, and thus, may compare the achievable stroke length to the minimum stroke length thereafter. Thus, in certain implementations, the system may only provide or update the indication of whether the target destination can be reached in response to the user releasing the admittance mode button.

At block 1940, the system receives an input from the user accepting the provided stroke length. For example, the system may be configured to receive using input that is indicative of whether the provided achievable stroke length is acceptable to the user. When the user accepts the provided achievable stroke length, the system may receive an input (e.g., a user intput) including an instruction for the system to move into the load instruments pose at block 1925. If the input received by the system indicates that the user has not accepted the achievable stroke length, the method ends at block 1950 and the system may display instructions to the user to reposition the cart to increase the achievable stroke length. However, in other embodiments, the system may be able to determine the a direction in which the first robotic arm may be moved to adjust the achievable stroke length such that the medical procedure can be performed; in such embodiments, the system may determine that the achievable stroke length is less than the minimum stroke length, calculate a direction from the current position to the boundary, and provide an indication of the direction from the current position to the boundary.

C. Simulation of Achievable Stroke Length.

In certain embodiments, to determine the achievable stroke length for an initial position of one or more robotic arms, the system may perform a simulation of the medical procedure. For example, a given medical procedure may include a set sequence of movements of the associated robotic arms that depend on the specific procedure involved. The sequence of movements may also depend on the characteristics of the patient depending on the medical procedure.

Figure 20:
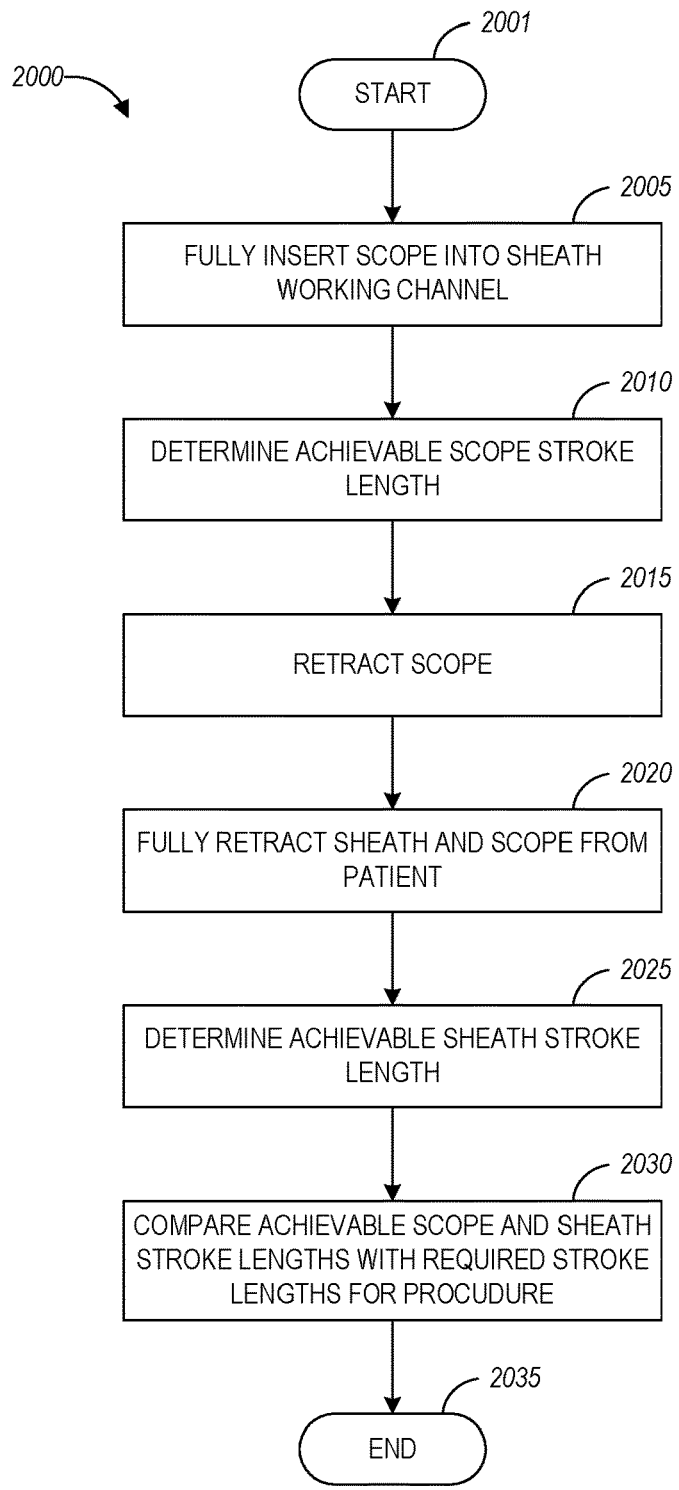
FIG. 20 is a flow-chart which illustrates an example methodology for simulating a medical procedure in accordance with aspects of this disclosure.

FIG. 20 is a flow-chart which illustrates an example methodology for simulating a medical procedure in accordance with aspects of this disclosure. In particular, the FIG. 20 embodiment relates to a bronchoscopy procedure. The specifics of a simulation will depend on the medical procedure being performed and the corresponding configuration of the surgical system including the number of robotic arms involved in the procedure, the alignment process, any additional device attached or installed in the patient, etc.

The method 2000 starts at block 2001. At block 2005, the system simulates full insertion of the leader into the sheath. Since the position of the sheath robotic arm is assumed to be in alignment with the access point (e.g., a patient introducer) for the purposes of the simulation, block 2005 corresponds to full insertion of both the sheath and leader into the patient. At block 2010, the system determines the achievable leader stroke length based on the results of the simulated insertion in block 2005. That is, if the simulation results in some sort of collision or other barrier to the leader being fully inserted into the sheath, the simulated achievable stroke length of the leader may be less than the maximum achievable leader stroke length under ideal conditions.

At block 2015, the system simulates retracting the leader from the sheath working channel. This may involve simulating the retraction of the leader to the initial pose of the leader robotic arm prior to the block 2005 simulation. At block 2020, the system simulates the full retraction of both the sheath and the leader from the patient. Here, full retraction may refer to retracting the sheath and leader fully from the patient, but leaving the sheath and leader in the access point. At block 2025, the system determines the achievable stroke length of the sheath based on the simulated results of block 2020. For example, if the system determines that a collision or other barrier would prevent the sheath being fully retracted from the patient, the simulated achievable stroke length of the sheath may be less than the maximum achievable sheath stroke length under ideal conditions.

At block 2030, the system compares the simulated achievable leader and sheath strokes lengths with the required stroke length(s) for the procedure. As described above, the system may be able to calculate the required stroke lengths for the procedure based on a pre-operative mapping of the patient's luminal network. The method 200 ends at block 2035.

The method 2000 described in connection with FIG. 20 includes a simulation of a bronchoscopy procedure. However, the sequence of movements during a specific medical procedure may be altered from the sequence described in connection with FIG. 20 depending on the requirements for performing the procedure. Similarly, the sequence of events may be simulated in orders other than shown in FIG. 20 as long as the achievable stroke lengths of the leader and sheath can be simulated.

In another example, the system may simulate the movement of first and second robotic arms in the same sequence as performed during a procedure. For example, the system may determine at least one first movement of the first robotic arm that facilitates advancing the sheath from the access point to the target region via the path. The system may also determine at least one second movement of the second robotic arm that facilitates advancing the leader through the sheath to the target region. Thereafter, the system may simulate the at least one first movement and the at least one second movement at a position of the first and second robotic arms and calculate at least one achievable stroke length of the first and second robotic arms based on the simulation.

Although the method 2000 has been described in connection with a bronchoscopy example, aspects of this disclosure can also simulate the achievable stroke length(s) for one or more robotic arms for other types of medical or surgical procedures. In certain implementations, the robotic system may be configurable to perform one of a plurality of surgical procedures. In these implementations, the system may be configured to receive an input indicative of a surgical procedure for the patient. Based on the received surgical procedure input, the system may determine at least one target movement of the first robotic arm that facilitates the advancing of the medical instrument from the access point to the target region via the path and performing the surgical procedure at the target region. This may be based on the surgical or medical instrument used to perform the procedure as well as the number of robotic arms required to manipulate the instrument. The system may also simulate the at least one target movement at the position of the first robotic arm and calculate an achievable stroke length of the first robotic arm based on the simulated movement.

The system may determine that the simulated movement would result in the first robotic arm colliding with an object. The object may be another portion of the surgical robotic system, such as another robotic arm, the cart, etc. or may be another object within the operating environment. In order to simulate collisions with other objects, the position and shape of object(s) within the operating environment may be programmed into the system's memory. For example, a C-arm may be used in various medical procedures and may be located within the working area of the robotic arms. Thus, the system may simulate whether a given procedure, based on the selected initial pose, would result in collision with the C-arm. The calculating of the achievable stroke length may be further based on the determination that the simulated movement would result in the first robotic arm colliding with the object and the determination of whether the simulated movement would result in the first robotic arm being fully extended.

The full extension of one or more of the robotic arms may also limit the stroke length of the corresponding arms. Thus, during simulation, the system may also determine whether the simulated movement would result in one of the robotic arms being fully extended. The system may further calculate of the achievable stroke length based on the determination that the simulated movement would result in the one of the robotic arms being fully extended.

In alternative implementations, rather than calculating or simulating the achievable stroke length in real-time, the system may store a stroke length validation module in memory that defines an achievable stroke length of the first robotic arm for each of a plurality of initial poses of the first robotic arm. The stroke length validation module may comprise a database or procedure, stored in memory, which relates values of initial poses of the first robotic arm to corresponding achievable stroke lengths. In certain embodiments, the stroke length validation module may comprise a look-up table, or other data structure, that stores an achievable stroke length for each of a plurality of initial poses of the first robotic arm. In other embodiments, the stroke length validation module may comprise a technique for calculating the achievable stroke length for a given initial pose of the robotic arm.

This may be practical for medical procedures that are well defined and in which there are no additional factors (e.g., object collisions) that can limit stroke length besides the initial pose of the first robotic arm. These implementations may include during the arm setup phase detecting a movement of the first robotic arm to the initial pose and retrieve an achievable stroke length from the stroke length validation module based on the initial pose. The system may then determine whether the achievable stroke length is greater than or equal to the minimum stroke length and provide an indication of whether the achievable stroke length is greater than or equal to the minimum stroke length. The system may also retrieve the achievable stroke length from the stroke length validation module in response to detecting a user-initiated event, such as a user input instructing the system to use the stroke length validation module in determining the achievable stroke length.

3. Implementing Systems and Terminology.

Implementations disclosed herein provide systems, methods and apparatus for determining whether an initial pose of a robotic arm will provide a sufficient stroke length for a medical procedure. This determination may include, in certain embodiments, a simulation of the procedure to determine the achievable stroke length of the robotic arm.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The calculation and determination functions for simulating and determining stroke length described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic system, comprising:
a first robotic arm comprising a distal end configured to manipulate a medical instrument through an access point of a patient, wherein the medical instrument comprises an elongate shaft configured to enter the patient through the access point;
a processor; and
a memory storing a boundary for an initial position of the distal end of first robotic arm, the boundary indicative of a space to which movement of the distal end of the first robotic arm is permitted for the initial position, the memory further storing computer-executable instructions, that when executed, cause the processor to:
during an arm setup phase, provide an indication of the boundary during movement of the distal end of the first robotic arm,
receive an input to override the boundary,
simulate, based on a current position of the distal end of the first robotic arm being located outside of the boundary, an achievable stroke length of the first robotic arm to facilitate advancing of the medical instrument from the access point to a target region within the patient, and
provide an indication that the simulated achievable stroke length reaches the target region.

2. The robotic system of claim 1, wherein:
the memory further stores a required stroke length for performing a specific medical procedure on the patient,
the memory further comprises computer-executable instructions, that when executed, cause the processor to:
compare the required stroke length to the achievable stroke length, and
provide of the indication that the simulated achievable stroke length reaches the target region comprises an indication that the achievable stroke length is greater than or equal to the required stroke length.

3. The robotic system of claim 2, wherein the memory further comprises computer-executable instructions, that when executed, cause the processor to:
determine that a second achievable stroke length is less than the required stroke length,
calculate a direction from the current position to the boundary, and
provide an indication of the direction from the current position to the boundary.

4. The robotic system of claim 1, wherein the memory further comprises computer-executable instructions, that when executed, cause the processor to:
provide the indication of the boundary via at least one of: a haptic indication, a visual indication, and an audio indication.

5. The robotic system of claim 1, further comprising:
an override input device configured to receive the input to override the boundary.

6. The robotic system of claim 1, wherein:
the first robotic arm comprises one or more sensors configured to generate a signal indicative of a force applied to the first robotic arm,
the memory further comprises computer-executable instructions, that when executed, cause the processor to:
receive the signal indicative of the force applied to the first robotic arm, and
align the first robotic arm with the access point of the patient based on the received signal.

7. The robotic system of claim 1, wherein the memory further comprises computer-executable instructions, that when executed, cause the processor to:
receive an input indicative of a surgical procedure for the patient, and
determine, based on the surgical procedure, at least one target movement of the first robotic arm that facilitates the advancing of the medical instrument from the access point to the target region via a path and performing the surgical procedure at the target region, wherein the simulation of the achievable stroke length of the first robotic arm is further based on the at least one target movement.

8. The robotic system of claim 1, wherein the memory further comprises computer-executable instructions, that when executed, cause the processor to:
determine that a simulated movement would result in the first robotic arm colliding with an object,
wherein the simulation of the achievable stroke length is further based on the determination that the simulated movement would result in the first robotic arm colliding with the object.

9. The robotic system of claim 1, wherein the memory further comprises computer-executable instructions, that when executed, cause the processor to:
determine that a simulated movement would result in the first robotic arm being fully extended,
wherein the simulation of the achievable stroke length is further based on the determination that the simulated movement would result in the first robotic arm being fully extended.

10. The system of claim 1, wherein:
the boundary comprises a boundary area, and
the memory further comprises computer-executable instructions to cause the processor to limit the movement of the first robotic arm within the boundary area during the arm setup phase.

11. A non-transitory computer readable storage medium having stored thereon instructions that, when executed, cause at least one computing device to:
during an arm setup phase, provide an indication of a boundary for an initial position of a distal end of a first robotic arm during movement of the first robotic arm, the distal end of the first robotic arm configured to manipulate an elongated shaft of a medical instrument through an access point of a patient, and the boundary indicative of a space to which movement of the distal end of the first robotic arm is permitted for the initial position;
receive an input to override the boundary;
simulate, based on a current position of the distal end of the first robotic arm being outside of the boundary, an achievable stroke length of the first robotic arm to facilitate advancing of the medical instrument from the access point to a target region within the patient, the simulated achievable stroke length being based on a simulation of a retraction of the distal end of the first robotic arm away from the current position and an insertion of the distal end of the first robotic arm towards the patient; and
provide an indication of the achievable stroke length.

12. The non-transitory computer readable storage medium of claim 11, further having stored thereon instructions that, when executed, cause at least one computing device to:
compare a required stroke length to the achievable stroke length for performing a specific medical procedure on the patient,
wherein the indication of the achievable stroke length comprises an indication of whether the achievable stroke length is greater than or equal to the required stroke length.

13. The non-transitory computer readable storage medium of claim 12, further having stored thereon instructions that, when executed, cause at least one computing device to:
determine that the achievable stroke length is less than a required stroke length;
calculate a direction from the current position to the boundary; and
provide an indication of the direction from the current position to the boundary.

14. The non-transitory computer readable storage medium of claim 11, further having stored thereon instructions that, when executed, cause at least one computing device to:
provide the indication of the boundary via at least one of: a haptic indication, a visual indication, and an audio indication.

15. The non-transitory computer readable storage medium of claim 11, further having stored thereon instructions that, when executed, cause at least one computing device to:
receive the input to override the boundary via an override input device.

16. The non-transitory computer readable storage medium of claim 11, further having stored thereon instructions that, when executed, cause at least one computing device to:
receive a signal indicative of a force applied to the first robotic arm from one or more sensors of the first robotic arm, the one or more sensors configured to generate the signal indicative of the force applied to the first robotic arm, and
align the distal end of the first robotic arm with the access point of the patient based on the received signal.

17. The non-transitory computer readable storage medium of claim 11, further having stored thereon instructions that, when executed, cause at least one computing device to:
receive an input indicative of a surgical procedure for the patient; and
determine, based on the surgical procedure, at least one target movement of the first robotic arm that facilitates the advancing of the medical instrument from the access point to the target region via a path and performing the surgical procedure at the target region,
wherein the simulation of the achievable stroke length of the first robotic arm is further based on the at least one target movement.

18. The non-transitory computer readable storage medium of claim 11, further having stored thereon instructions that, when executed, cause at least one computing device to:
determine that a simulated movement would result in the first robotic arm colliding with an object,
wherein the simulation of the achievable stroke length is further based on the determination that the simulated movement would result in the first robotic arm colliding with the object.

19. The non-transitory computer readable storage medium of claim 11, further having stored thereon instructions that, when executed, cause at least one computing device to:
determine that the simulated movement would result in the first robotic arm being fully extended,
wherein the simulation of the achievable stroke length is further based on the determination that the simulated movement would result in the first robotic arm being fully extended.

20. The non-transitory computer readable storage medium of claim 11, wherein:
the boundary comprises a boundary area, and
the non-transitory computer readable storage medium further has stored thereon instructions that, when executed, cause at least one computing device to limit the movement of the distal end of the first robotic arm within the boundary area during the arm setup phase.

21. A method of positioning a first robotic arm, the method comprising:

during an arm setup phase, providing an indication of a boundary for an initial position of a distal end of the first robotic arm during movement of the first robotic arm, the distal end of the first robotic arm configured to manipulate an elongated shaft of a medical instrument through an access point of a patient, and the boundary indicative of a space to which movement of the distal end of the first robotic arm is permitted for the initial position;

receiving an input to override the boundary;

simulating, based on a current position of the distal end of the first robotic arm being outside of the boundary, an achievable stroke length of the first robotic arm to facilitate advancing of the medical instrument from the access point to a target region within the patient; and providing an indication that the simulated achievable stroke length reaches the target region.

22. The method of claim 21, further comprising:

comparing a required stroke length to the achievable stroke length for performing a specific medical procedure on the patient, wherein the providing of the indication that the achievable stroke length reaches the target region comprises providing an indication that the achievable stroke length is greater than or equal to the required stroke length.

23. The method of claim 22, further comprising:

determining that a second achievable stroke length is less than the required stroke length;

calculating a direction from the current position to the boundary; and providing an indication of the direction from the current position to the boundary.

24. The method of claim 21, further comprising:

providing the indication of the boundary via at least one of: a haptic indication, a visual indication, and an audio indication.

25. The method of claim 21, further comprising:

receiving the input to override the boundary via an override input device.

26. The method of claim 21, further comprising:

receiving a signal indicative of a force applied to the first robotic arm from one or more sensors of the first robotic arm, the one or more sensors configured to generate the signal indicative of the force applied to the first robotic arm, and aligning the distal end of the first robotic arm with the access point of the patient based on the received signal.

27. The method of claim 21, further comprising:

receiving an input indicative of a surgical procedure for the patient; and determining, based on the surgical procedure, at least one target movement of the first robotic arm that facilitates the advancing of the medical instrument from the access point to the target region via a path and performing the surgical procedure at the target region, wherein the simulating of the achievable stroke length of the first robotic arm is further based on the at least one target movement.

28. The method of claim 21, further comprising:

determining that a simulated movement would result in the first robotic arm colliding with an object, wherein the simulating of the achievable stroke length is further based on determining that the simulated movement would result in the first robotic arm colliding with the object.

29. The method of claim 21, further comprising:

determining that a simulated movement would result in the first robotic arm being fully extended, wherein the simulating of the achievable stroke length is further based on determining that the simulated movement would result in the first robotic arm being fully extended.

30. The method of claim 21, wherein:

the boundary comprises a boundary area, and the method further comprises limiting the movement of the first robotic arm within the boundary area during the arm setup phase.

* * * * *